(12) United States Patent
Liang et al.

(10) Patent No.: US 11,622,883 B2
(45) Date of Patent: Apr. 11, 2023

(54) PATIENT TEMPERATURE AND BLOOD FLOW MANAGEMENT

(71) Applicant: Flotherm, Inc., Los Angeles, CA (US)

(72) Inventors: Bradley C Liang, Bloomfield Hills, MI (US); Abhinav Ramani, Los Angeles, CA (US); Brian T. Kannard, Los Angeles, CA (US); Peter Luke Santa Maria, Redwood City, CA (US); Scott Janis, San Francisco, CA (US); Colton Sanford, San Francisco, CA (US); Isamu Taguchi, San Francisco, CA (US)

(73) Assignee: Flotherm, Inc., Los Angeles, CA (US)

( * ) Notice: Subject to any disclaimer, the term of this patent is extended or adjusted under 35 U.S.C. 154(b) by 485 days.

(21) Appl. No.: 16/777,894

(22) Filed: Jan. 31, 2020

(65) Prior Publication Data

US 2020/0246180 A1 Aug. 6, 2020

Related U.S. Application Data

(60) Provisional application No. 62/799,479, filed on Jan. 31, 2019.

(51) Int. Cl.
*A61F 7/02* (2006.01)
*A61F 7/00* (2006.01)

(52) U.S. Cl.
CPC ........ *A61F 7/02* (2013.01); *A61F 2007/0043* (2013.01); *A61F 2007/0045* (2013.01); *A61F 2007/0047* (2013.01); *A61F 2007/0091* (2013.01); *A61F 2007/0247* (2013.01)

(58) Field of Classification Search
CPC ...... A61F 2007/0041; A61F 2007/0042; A61F 2007/0043; A61F 2007/0045; A61F 2007/0047; A61F 2007/0054; A61F 2007/0071; A61F 2007/0091; A61F 2007/0228; A61F 2007/0247; A61F 7/007; A61F 7/02

See application file for complete search history.

(56) References Cited

U.S. PATENT DOCUMENTS

| | | |
|---|---|---|
| 267,435 A | 11/1882 | Leiter |
| 4,029,087 A | 6/1977 | Dye |
| 4,107,509 A | 8/1978 | Scher |
| 4,624,244 A | 11/1986 | Taheri |
| 4,865,020 A | 9/1989 | Bullard |
| 5,411,541 A | 5/1995 | Bell |
| 5,626,556 A | 5/1997 | Tobler et al. |
| 5,674,262 A | 10/1997 | Tumey |
| 6,254,554 B1 | 7/2001 | Turtzo |
| 6,387,065 B1 | 5/2002 | Tumey |
| 7,074,177 B2 | 7/2006 | Pickett |
| 7,196,289 B2 | 3/2007 | Ellis et al. |

(Continued)

FOREIGN PATENT DOCUMENTS

EP 0303029 A1 2/1989

*Primary Examiner* — Tigist S Demie
(74) *Attorney, Agent, or Firm* — Chang & Hale LLP

(57) ABSTRACT

Systems for maintaining normothermia in a patient via compression and warming are disclosed and include a first warming element configured to apply warming to the popliteal fossa, a second warming element configured to apply warming to the sole of the foot, and a compression element configured to apply compression to the calf.

10 Claims, 23 Drawing Sheets

(56) References Cited

U.S. PATENT DOCUMENTS

| | | |
|---|---|---|
| 7,972,287 B2 | 7/2011 | Stewart |
| 8,034,007 B2 | 10/2011 | Avitable |
| 8,162,863 B2 | 4/2012 | Nardi |
| 8,454,542 B2 | 6/2013 | Hirata |
| 8,603,150 B2 | 12/2013 | Kane |
| 9,033,906 B2 | 5/2015 | Nolan |
| 9,144,530 B2 | 9/2015 | Davis |
| 2004/0210176 A1 | 10/2004 | Diana |
| 2005/0075531 A1 | 4/2005 | Loeb |
| 2005/0103353 A1 | 5/2005 | Grahn |
| 2005/0126578 A1 | 6/2005 | Garrison |
| 2007/0135743 A1 | 6/2007 | Meyer |
| 2008/0021531 A1 | 1/2008 | Kane et al. |
| 2008/0064992 A1 | 3/2008 | Stewart et al. |
| 2008/0161891 A1* | 7/2008 | Pierre ............... A61F 7/02 607/107 |
| 2009/0069731 A1 | 3/2009 | Parish |
| 2009/0177184 A1 | 7/2009 | Christensen |
| 2009/0221943 A1* | 9/2009 | Burbank ............ A61N 1/36021 601/46 |
| 2009/0270910 A1 | 10/2009 | Hargens |
| 2010/0042026 A1 | 2/2010 | Kloecker |
| 2010/0076356 A1 | 3/2010 | Biondo |
| 2010/0152821 A1 | 6/2010 | Rein et al. |
| 2010/0210982 A1 | 8/2010 | Balachandran |
| 2011/0004132 A1 | 1/2011 | Cook |
| 2011/0098792 A1* | 4/2011 | Lowe ............... A61F 7/0085 607/104 |
| 2011/0190675 A1 | 8/2011 | Vess |
| 2011/0251536 A1 | 10/2011 | Wilford et al. |
| 2012/0065561 A1 | 3/2012 | Ballas et al. |
| 2012/0065664 A1 | 3/2012 | Avitable et al. |
| 2013/0030331 A1* | 1/2013 | Quisenberry ............. A61F 7/02 601/18 |
| 2013/0324895 A1 | 12/2013 | Avitable et al. |
| 2014/0207036 A1 | 7/2014 | Perry et al. |
| 2014/0222121 A1 | 8/2014 | Spence |
| 2014/0276257 A1* | 9/2014 | Santa Maria ......... A61H 9/005 601/18 |
| 2015/0290065 A1 | 10/2015 | Augustine et al. |
| 2017/0135855 A1 | 5/2017 | Stefan et al. |
| 2017/0258628 A1 | 9/2017 | Awasthi |
| 2018/0271696 A1 | 9/2018 | Santa Maria et al. |
| 2020/0245950 A1 | 8/2020 | Liang et al. |
| 2020/0246180 A1 | 8/2020 | Liang et al. |

\* cited by examiner

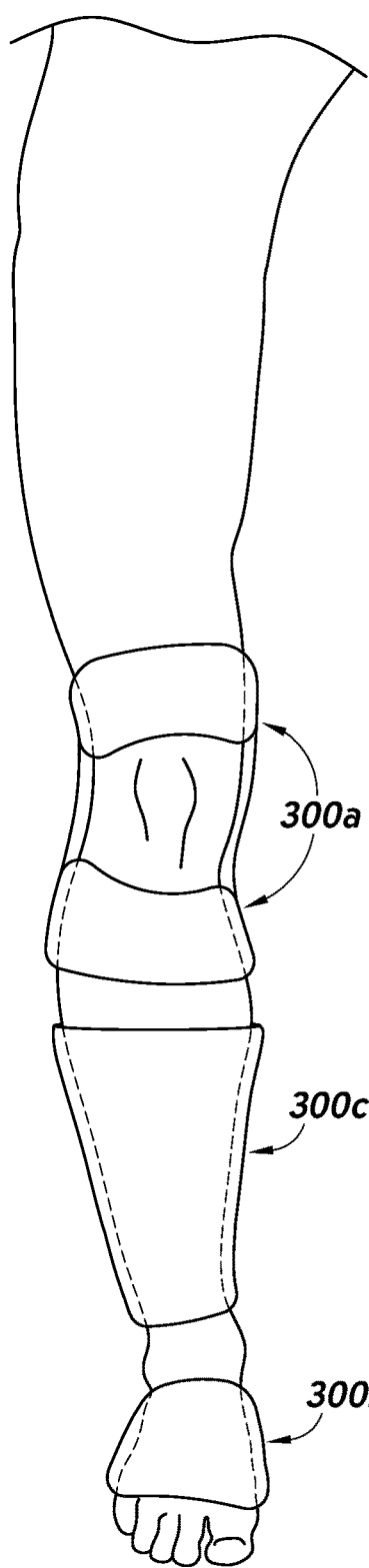
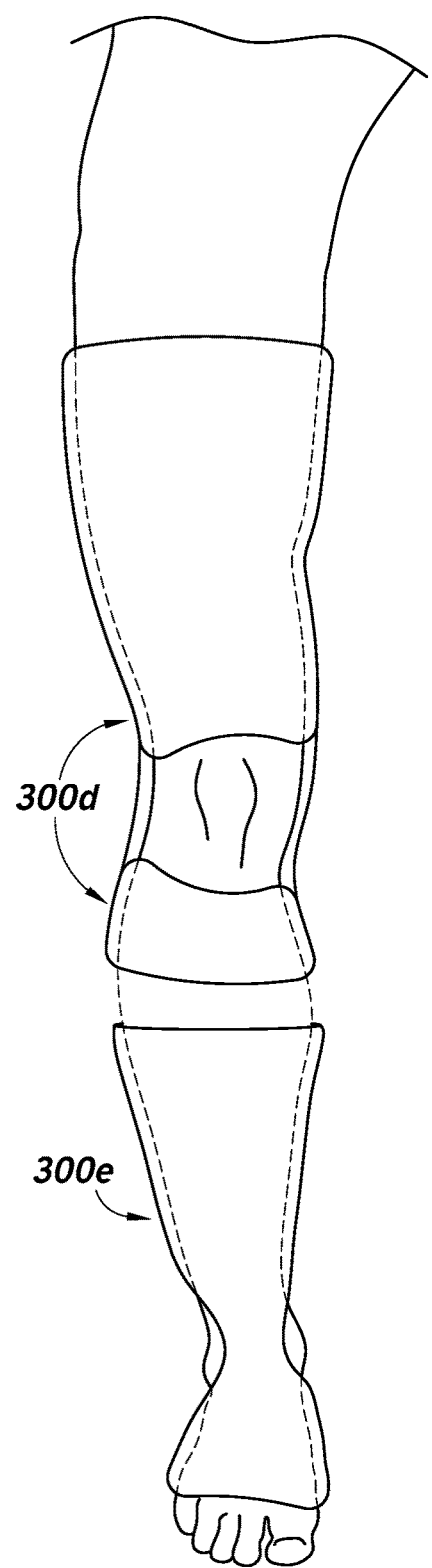
FIG. 3A
FIG. 3B

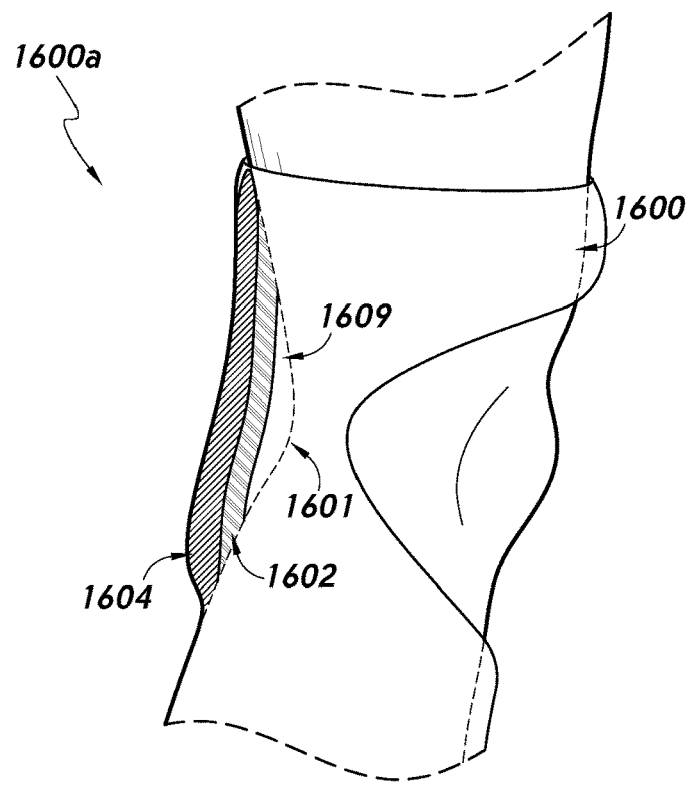
FIG. 16
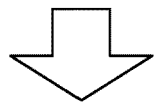
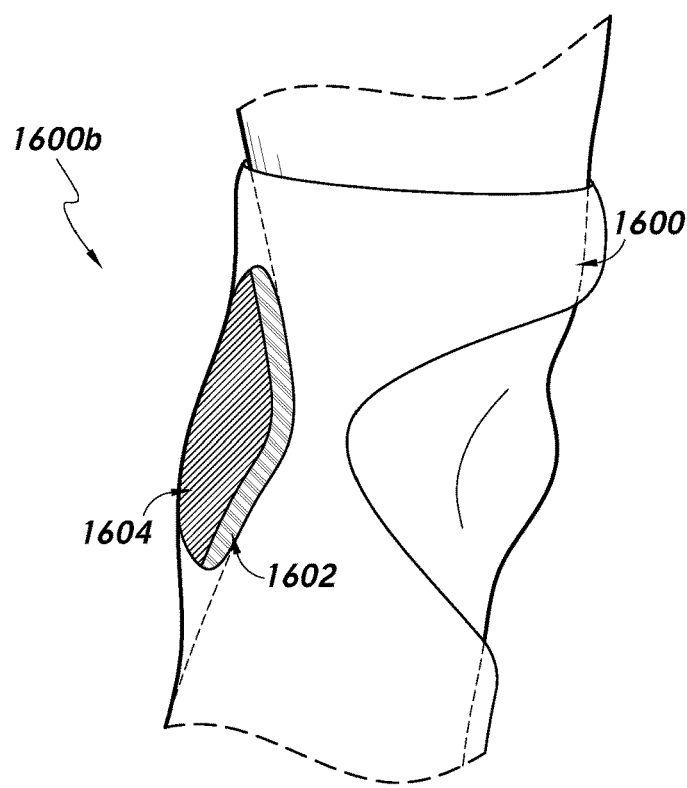

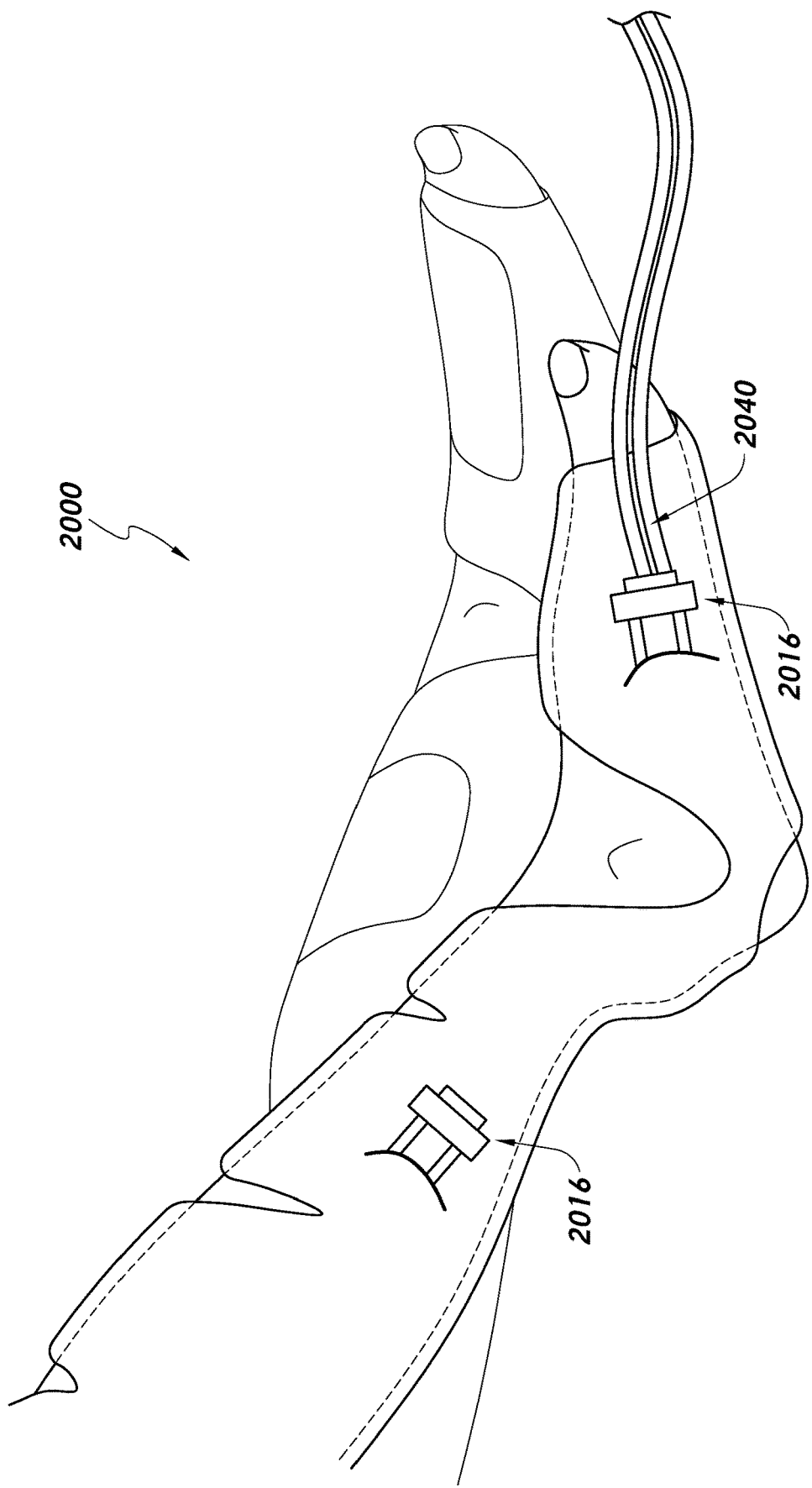

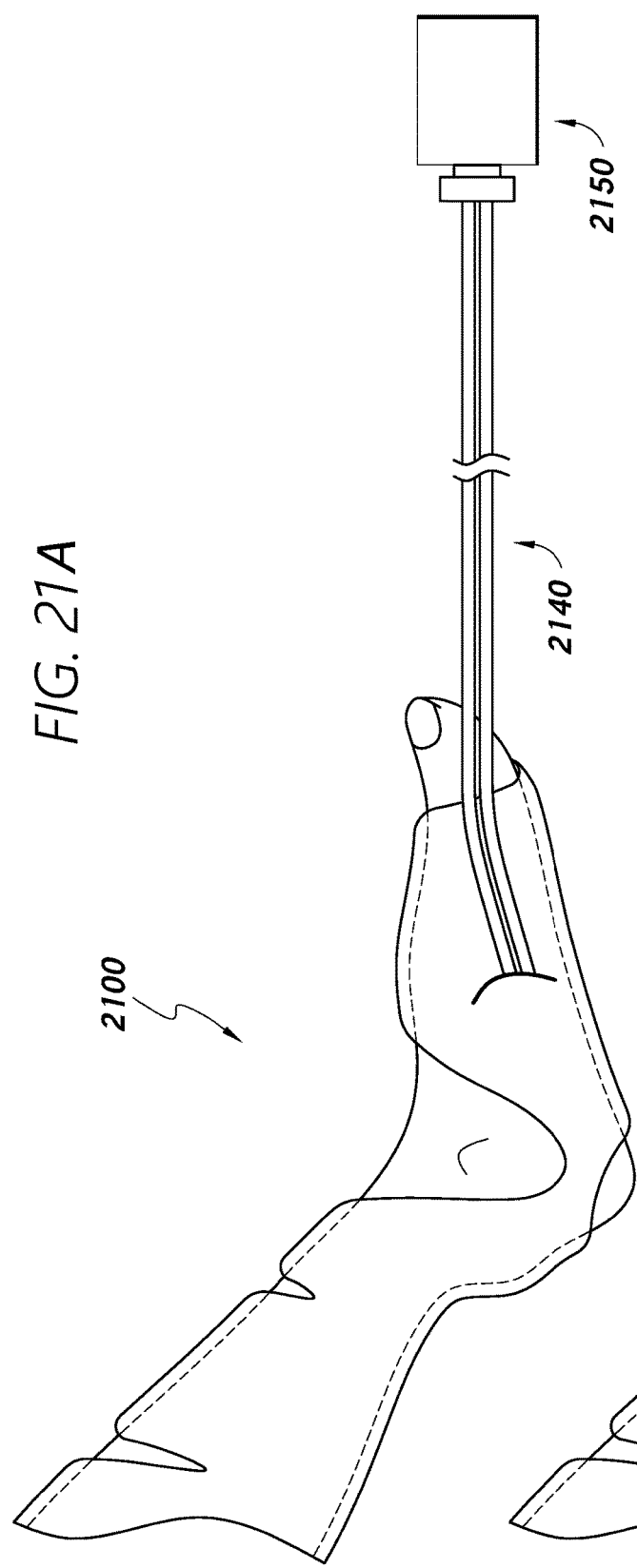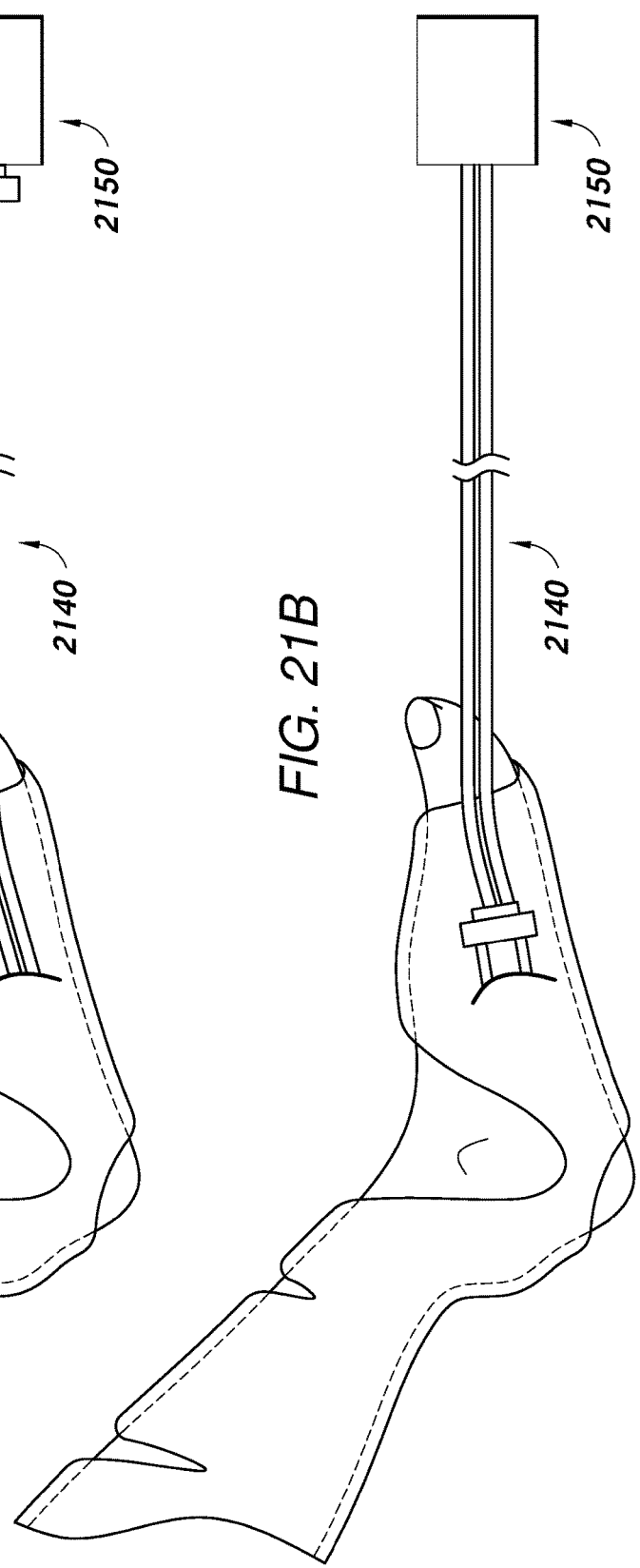

PATIENT TEMPERATURE AND BLOOD FLOW MANAGEMENT

RELATED APPLICATION

This application claims priority to U.S. Provisional Application No. 62/799,479, filed on Jan. 31, 2019, entitled DEVICE FOR ENHANCING BLOOD FLOW AND MAINTAINING NORMOTHERMIA, the disclosure of which is hereby incorporated by reference in its entirety.

BACKGROUND

Field

The present application relates to medical devices and methods. More specifically, the application relates to methods, devices and systems for regulating body temperature of a mammal.

Description of Related Art

Each year, over 60 million surgical procedures are performed in the United States. Patient temperatures can drop precipitously during surgery, due to the effects of general anesthesia, lack of insulating clothing, and exposure to cold operating room temperatures.

SUMMARY

Described herein are one or more methods and devices for maintaining normothermia via compression and warming. In some implementations of the present disclosure, a system comprises a first warming element configured to apply warming to the popliteal fossa, a second warming element configured to apply warming to the sole of the foot and a compression element configured to apply compression to the calf.

Some implementations of the present disclosure relate to a system for maintaining normothermia via compression and warming, the system comprising a first warming element configured to apply warming to the popliteal fossa and/or other portion of a patient's body, a second warming element configured to apply warming to the sole of the foot and/or other portion of the patient's body, and a compression element configured to apply compression to the calf.

The first warming element may be configured to apply warming to the popliteal fossa and sole of the foot via conductive means. In some embodiments, warming is applied to the popliteal fossa and sole of the foot through the use of resistive heating. Warming may be applied to the popliteal fossa and sole of the foot through the use of a fluid-warmed bladder. In some embodiments, contact between the first warming element and the popliteal fossa is maintained through the use of a limb-biasing apparatus. The limb-biasing apparatus may comprise one or more of a foam element, a bladder, and a strap positioned between the warming element and an outer sleeve layer. In some embodiments, the limb-biasing apparatus is configured to cause the first warming element to be pressed against the popliteal fossa to establish direct surface contact between the warming element and the popliteal fossa.

In some embodiments, warming is applied to the popliteal fossa and sole of the foot via convective means. Thermally-treated gas or fluid may be provided to the first warming element and the second warming element by way of an air-tight and water-tight hose. In some embodiments, the air-tight and water-tight hose comprises a warming unit for providing a stream of temperature-regulated fluid through channels or bladders. The air-tight and water-tight hose may comprise a heater in the warming unit. In some embodiments, the air-tight and water-tight hose comprises a control circuit in the warming unit. The air-tight and water-tight hose may comprise a limb sleeve with perforation connected to the warming unit. In some embodiments, warming temperature of the first warming element and the second warming element is cyclical so to avoid burning of the skin. The first warming element and the second warming element may be configured to deliver heat that is controlled via pulse-width modulation. In some embodiments, the first warming element and the second warming element are configured to utilize a heat application cycle that may be synced (with some offset) in time to compression cycles of the compression element.

Some implementations of the present disclosure relate to a limb sleeve comprising a first anomaly indicative of knee placement, a second anomaly indicative of heel placement, and a first extendable and collapsible section configured to facilitate placement of the first anomaly and the second anomaly.

In some embodiments, the first extendable and collapsible section comprises an adjustable region to enable the first anomaly and the second anomaly to be stretched prior to application. The first extendable and collapsible section may comprise a self-adhering region. In some embodiments, the first anomaly and the second anomaly comprise one or more of physical, visible, or palpable features.

Some implementations of the present disclosure relate to a connector between a limb sleeve and a controller, the connector comprising an interface configured to create a hermetic seal between at least one of an internal fluid channel and an electric channel and maintain the hermetic seal to an external environment.

The interface may be configured to attach in either of two possible fixation orientations. In some embodiments, the interface can only be attached in a single orientation. The interface may be configured to create a hermetic seal between only one of the internal fluid channel and the electric channel.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements. However, it should be understood that the use of similar reference numbers in connection with multiple drawings does not necessarily imply similarity between respective embodiments associated therewith. Furthermore, it should be understood that the features of the respective drawings are not necessarily drawn to scale, and the illustrated sizes thereof are presented for the purpose of illustration of inventive aspects thereof. Generally, certain of the illustrated features may be relatively smaller than as illustrated in some embodiments or configurations.

FIGS. 3A and 3B provide front views of a non-continuous sleeve configured to provide blood flow and/or compression therapy to a patient.

FIG. 16 provides side views of an inflatable sleeve in a deflated state and in an inflated state in accordance with one or more embodiments.

FIG. 20 illustrates sleeve comprising inlets configured to connect to a controller via an interface in accordance with one or more embodiments.

FIGS. 21A and 21B illustrate systems including one or more cable components connecting a sleeve to a controller in accordance with one or more embodiments.

DETAILED DESCRIPTION

Figure 1:
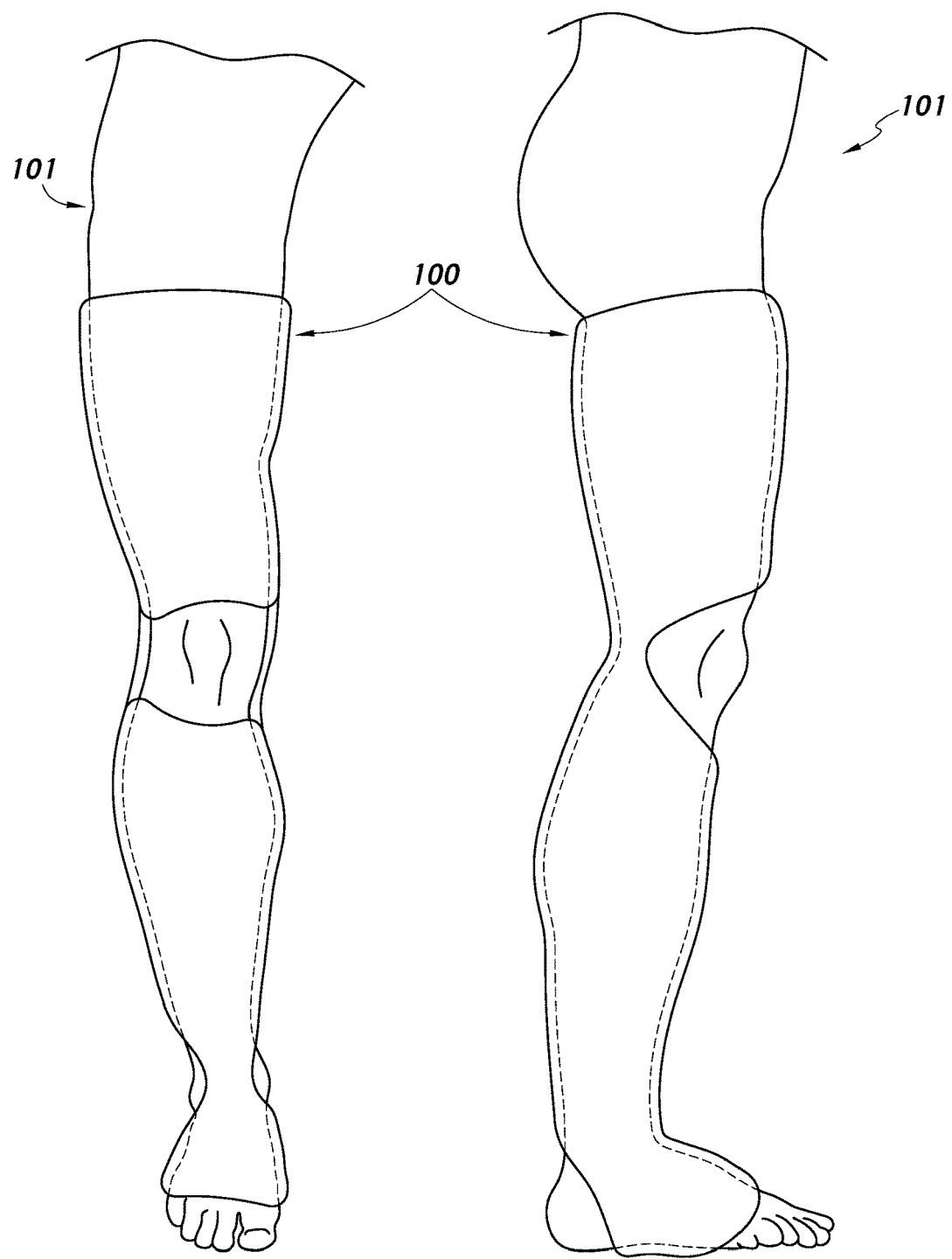
FIG. 1 provides front and side views of a sleeve configured to provide blood flow and/or compression therapy to a patient.

The headings provided herein are for convenience only and do not necessarily affect the scope or meaning of the claimed invention.

Overview

Each year, over 60 million surgical procedures are performed in the United States. While great care may be taken to prevent surgical complications, one commonly overlooked and under-addressed problem is the risk of developing hypothermia before, during, or after surgery (referred to as "inadvertent perioperative hypothermia" or "IPH"). Patient temperatures can drop precipitously during surgery due to the effects of general anesthesia, lack of insulating clothing, and exposure to cold operating room temperatures. Even with today's standard of care, 30-50% of surgical patients may develop hypothermia.

Hypothermia often causes much more than patient discomfort. Patients who suffer even mild IPH can face a significantly elevated risk of developing surgical site infections, cardiac morbidities, intraoperative bleeding, and other avoidable complications. Together, these complications can significantly increase recovery time and overall length of hospital stay, leading to increased costs for all parties. By some estimates, the unmanaged risk for IPH is a $15 billion problem in the United States alone, and yet it is largely overlooked.

Perioperative heat loss can occur predominantly via convective heat transfer, particularly through the palms of the hands, soles of the feet, and exposed surgical site surface area. During preoperative care, patients are often dressed solely in a gown and are often exposed to relatively cold waiting areas with little to no insulation. Although patients are generally only anesthetized at the start of surgery, patients often arrive at the surgical theater moderately hypothermic. This can put a patient at greater risk for developing severe hypothermia once anesthesia has been administered. Postoperative drops in core temperature can increase the likelihood of developing additional comorbidities, such as morbid cardiac outcomes, surgical site infections, and blood loss, any of which can prolong recovery and hospitalization.

Patients undergoing surgery can develop hypothermia during the surgical procedure itself, especially when the procedure involves the patient's core area, such as procedures involving the posterior or anterior sides of the thoracic, abdominal, and pelvic regions. Surgeries of the core involve the exposure of vital internal organs to the colder environment and thus carry a greater risk of hypothermia. Furthermore, core surgeries often necessitate uncovering of the trunk and chest, which render blankets and many other currently-available interventions inadequate. Once in the operating room, patients may be naked and exposed to a room temperature well below 36 degrees Celsius and to cold liquids used to wash the surgical site during sterilization preparation. At the onset of surgery, delivered anesthetics can immediately impair the normal autonomic thermoregulatory controls. Colder blood may be transferred from the peripheries of the body to the core through a phenomenon known as redistributive hypothermia. Vasodilatation and reduction in muscle tone can cause a significant drop in core temperature within the first half-hour of surgery.

Overall, compared to non-hypothermic patients, those who suffer from IPH experience greater rates of surgical site infections, bleeding, and cardiac complications. Such issues may require additional monitoring and/or increase the length of stay and/or subjective discomfort. The development of IPH is strongly correlated with a multitude of physiological organ system changes impacting the cardiovascular, respiratory, neurologic, immunologic, hematologic, drug-metabolic, and wound-healing mechanisms. The incidence of several post-surgical complications can be increased due to even mild hypothermia.

Intraoperatively, hypothermia can cause a decrease in cardiac output and heart rate, which can lead to ventricular dysrhythmias. Platelet functions can become impaired and there can be a decrease in coagulation factors, which can, in turn, lead to greater intraoperative bleeding and blood loss. Impaired immune functions can increase the rate of surgical site infections. Hypothermia is associated with a four-fold increase in surgical wound infection and twice as many morbid cardiac events. In select procedures such as colorectal, gynecologic, or spinal surgery, where infection rates are normally higher than other surgeries, hypothermia can be exceedingly dangerous to the intraoperative and postoperative recovery. These complications and others are supported in multiple studies and can result in both clinical and economic burdens.

Current methods of preventing hypothermia may not be completely effective. Even with the current interventions, up to 46% of patients are reported to be hypothermic at the start of surgery, and 33% are hypothermic upon arrival to the post-anesthesia care unit (PACU). Assuming the cost savings for maintaining normothermia in one patient is approximately $5.000 per patient, and approximately 30% of the 17 million high-risk surgical patients are hypothermic, a system-wide cost savings of $15 billion could be realized by keeping these patients normothermic. With rising healthcare costs and recent initiatives mandating the maintenance of perioperative normothermia, hospital administrators nationally are in need of new, efficacious and cost-effective devices to address perioperative hypothermia, a product space that has seen little innovation since the introduction of the forced-air warming blanket nearly three decades ago.

Some devices for perioperative warming may include forced-air temperature management devices (e.g., warming blankets). Some temperature management solutions utilize high-heat transfer conduction heating blankets and intraoperative hand-warming devices. However, such solutions can be associated with various key shortcomings including, for example: (1) undesirably high risk of contaminating the surgical field (e.g., forced-air methods can blow bacteria-containing air into the surgical field); (2) forced-air devices can get in the way (e.g., to warm the core, forced-air blankets may need to be in contact with the core, which may be near to the surgical site); and (3) operating room staff may turn down the temperature on a device due to their own comfort (e.g., staff members may turn down the patient's forced-air device due to the device heating the surrounding air). Moreover, certain devices may not be used in preoperative warming for one or more of the following reasons, among others: (1) some devices may immobilize the upper limbs, impeding patient mobilization; (2) devices may be cumbersome (e.g., a device may float on the patient and get blown off or fall off during use and/or transport, and they require large, predominantly floor-based blowers that may not be mobile; (3) they may not attach to the patient and/or can become dislodged during transport and obstruct the bed and other monitors and devices; and (4) they can require a conscious administrative decision to implement.

Embodiments of the present disclosure advantageously provide certain improved methods and systems for maintaining a patient's core body temperature before, during, and/or after surgery. Furthermore, embodiments described herein provide methods and systems for core body temperature management in an unobtrusive, effective, and easy-to-use (e.g., easy to set-up) manner. Some embodiments of the present disclosure can be suitable for use before, during, and/or after a surgical procedure and can be acceptable to the patient while awake in the preoperative and/or postoperative settings.

In some embodiments, lower limbs of patients may be leveraged to provide therapy and/or enable mobility. For example, some devices described herein may provide flexibility and/or one or more spaces around a knee, ankle, and/or other portions of a patient's body to allow the patient to flex and/or extend the limbs. Such patient mobility may provide a variety of benefits, including allowing patients to stand up to use the restroom without removing and reapplying the device.

Some embodiments of temperature management devices disclosed herein may be configured to provide warming to one or more arteries and/or veins passing along the patient's lower limbs, for example along the calf. Moreover, some embodiments may involve compression of one or more portions of the patient's body. For example, compression may be applied to the patient's calf. In some embodiments, compression may be performed in a sequential and/or gradient manner.

Limb Sleeve Devices

In some implementations, the present disclosure relates to devices, systems and methods directed toward delivering warming therapy and/or blood flow therapy to a patient to help reduce blood stasis, deep vein thrombosis, and/or pulmonary emboli and/or to help regulate body temperature and/or optimize blood circulation. Warming and/or blood flow therapy can be used in the systems, devices, and methods described herein to help maintain normothermia and/or help return circulation to a body's core, including the heart and lungs, from one or more extremities/limbs. Blood flow therapy and/or blood circulation therapy may be accomplished in a number of different ways, including but not limited to intermittent compression. For example, in some implementations, intermittent compression may be performed through the execution of circumferential compression of one or more limbs. Warming therapy may likewise be accomplished in a variety of different ways, including without limitation through the use of ultrasound, electrical, mechanical, chemical, radiative and/or convective energy.

FIG. 1 provides front and side views of a temperature management sleeve 100 configured to provide blood flow and/or compression therapy to a patient. The term "sleeve" is used herein according to its plain and ordinary meaning and may refer to any device configured to be administered to one or more areas of a human body for delivery of heat and/or compression to the human body. For example, a "sleeve" may be a device configured to provide therapy to a limb or other body part at least in part through physical contact with the skin and/or other feature(s) of the body, wherein such physical contact provides therapy in and of itself or facilitates the provision of therapy through physically securing, positioning, or otherwise arranging one or more therapeutic devices, components, or features coupled to or otherwise associated with the sleeve. In some embodiments, the sleeve 100 may comprise a single continuous form or device and/or may be configured to apply therapy to a patient's thigh, knee, calf, and/or foot, and/or one or more other lower limb portions of a patient's body. The sleeve 100 may be applied to a patient's limb 101 (e.g., a leg, arm, and/or foot) and/or may be configured to deliver warming and/or to apply blood flow therapy to at least one area of the patient's limb 101. In some embodiments, the sleeve 100 may be configured to deliver heat to a majority of, or even the entire, limb 101 in conjunction with blood flow therapy. In some embodiments, the sleeve 100 may be configured to deliver heat to at least two different areas on the limb 101 while applying blood flow therapy between, adjacent to, and/or or overlapping the same areas.

Figure 2:
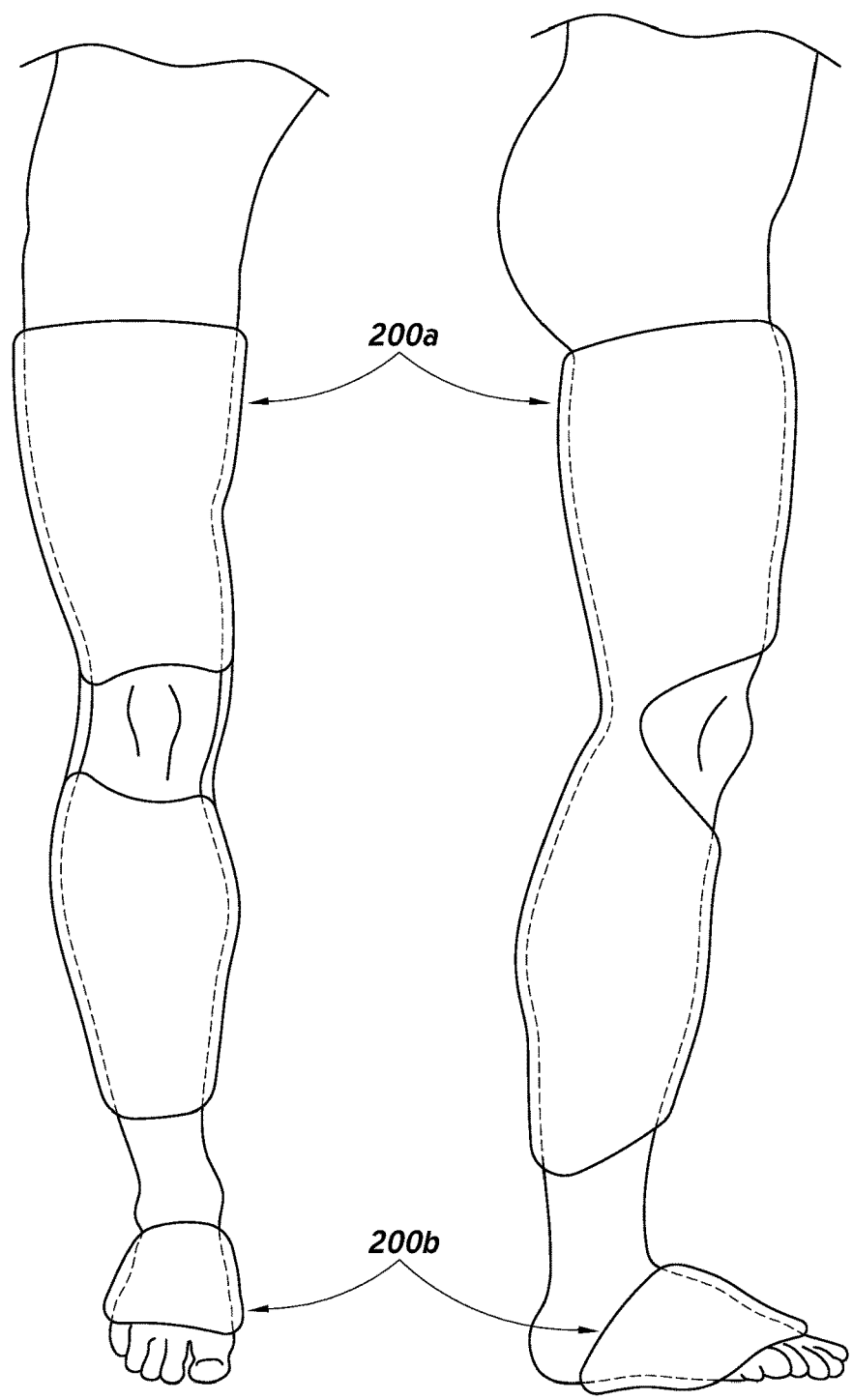
FIG. 2 provides front and side views of a non-continuous sleeve configured to provide blood flow and/or compression therapy to a patient.

FIG. 2 provides front and side views of a non-continuous sleeve configured to provide blood flow and/or compression therapy to a patient. The non-continuous sleeve may comprise at least two separate portions, which may include an upper portion 200a (e.g., configured to apply therapy to the patient's, thigh, popliteal fossa, and/or calf) and/or a lower portion 200b (e.g., configured to apply therapy to the sole of the patient's foot). In some embodiments, warming and/or compression therapy may be provided to a limb using either, but not both, of an upper portion and a lower portion, wherein such sleeve portion is configured to provide warming and/or compression functionality in accordance with aspects of the present disclosure.

FIGS. 3A and 3B provide front views of non-continuous temperature management sleeves configured to provide blood flow and/or compression therapy to a patient. In the embodiment shown in FIG. 3A, a first portion 300a and/or a second portion 300b of the sleeve may be configured to deliver heat to an anatomical area over and/or comprising the popliteal artery and/or an anatomical area over and/or comprising the medial and/or lateral plantar arteries, while a third portion 300c of the sleeve may be configured to deliver blood flow therapy through intermittent compression to an area between the first portion 300a and the second portion 300b. In some embodiments, the second portion 300b and third portion 300c may be combined into a single continuous portion (300d in FIG. 3B). For example, in the embodiment shown in FIG. 3B, heat and/or blood flow therapy may be applied by the second portion 300e to at least some portions of the patient's foot and/or calf area. That is, rather than separate sleeve portions for each of the lower leg and the foot, a single sleeve portion/form may cover the lower leg and foot and provide warming and/or compression therapy thereto. In some embodiments, warming and/or compression therapy may be provided to a limb using any single one, or combination, of an upper portion, lower leg portion, and/or foot portion, wherein each of such sleeve portion(s) is/are configured to provide warming and/or compression functionality in accordance with aspects of the present disclosure.

With further reference to FIG. 3A, in some embodiments, the first portion 300a, second portion 300b, and/or third portion 300c may be configured to provide heat and/or compression. In some embodiments, (e.g., in the example shown in FIG. 3B), the upper portion 300d may be configured to extend along a patient's thigh to provide heat and/or compression to the patient's thigh. The upper portion 300a/300d may be configured to apply heat to at least a popliteal fossa portion of (e.g., behind) the patient's knee area.

Forced gas and/or fluid delivered through the knee/upper leg portion 300a/300d, calf portion 300c/300e, and/or foot portion 300b/300e may be configured to apply compression to one or more areas of the patient's body. In some embodiments, forced gas and/or fluid moving through one or more portions for compression may be heated to also or alternatively provide heating. However, in some embodiments, one or more portions of the sleeve may comprise separate channels for compression gas and/or fluid and heated gas and/or fluid.

In some embodiments, heating may only be applied to certain areas of the patient's limb (e.g., at the popliteal fossa of the knee but not at the kneecap). However, heating may alternatively be applied across the entire sleeve or portions of sleeve. In some embodiments, forced gas and/or fluid passing through one or more portions of the sleeve(s) may be configured to circulate within the sleeve and/or to exit the sleeve. The sleeve(s) may comprise one or more perforations to allow gas and/or fluid to exit the sleeve.

Portions of the sleeve(s) may be composed of or comprise one or more of a variety of fabrics and/or materials. In some embodiments, one or more portions of the sleeve(s) configured to interface with the patient's skin may be at least partially composed of hydrogel, mesh, and/or other materials. The sleeve(s) may be at least partially composed of a breathable material. For example, an inner layer or layers of the sleeve(s) may comprise at least partially breathable/porous material to facilitate the egress of warm gas and/or fluid in the direction of the patient's skin. In some embodiments, the sleeve(s) may comprise one or more flexible sheets and/or circuits. For example, such sheets/circuits may have certain conductive traces printed/disposed thereon, wherein such traces may have electrical current passed therethrough to generate resistive heating for temperature management according to aspects of the present disclosure. The sleeve(s) may be sized and/or positioned to minimize overall space covering the patient's body while maximizing heat and/or compression therapy applied to the patient's body.

Some embodiments of the present disclosure provide various advantages and/or benefits over alternative temperature management solutions, including cost benefits. For example, some sleeves described herein may require heating at only a knee portion and/or a foot portion of a patient's body to provide core heating to the patient. This may limit the number of required heating elements and/or energy exhausted for heat transfer/generation, thereby providing relatively reduced cost. Moreover, for each area of the patient's body where heating is delivered, the heated area may require monitoring to prevent burning and/or ensure sufficient heating/warming. For example, certain embodiments described herein may comprise one or more temperature sensors at the knee portion and/or foot portion. Thus, by reducing the amount of heated portions of a sleeve device/assembly and/or the patient's anatomy, the amount of monitoring necessary to sufficiently evaluate the risk of overheating/burning may be reduced as well. Moreover, heating and/or monitoring may be less precise as the surface heating area increases. For example, devices may comprise an inlet for heated gas and/or fluid to enter the sleeve; the temperature at and/or near the inlet may be higher than at other portions of the sleeve and/or at an outlet of the sleeve. The larger the area covered by one or more heating bladders/elements of the sleeve, the lower the uniformity of the temperature throughout the one or more heating bladders/ elements. Thus, heating and/or monitoring precision may be improved as a result of the reduced heating area of the described embodiments.

Figure 4:
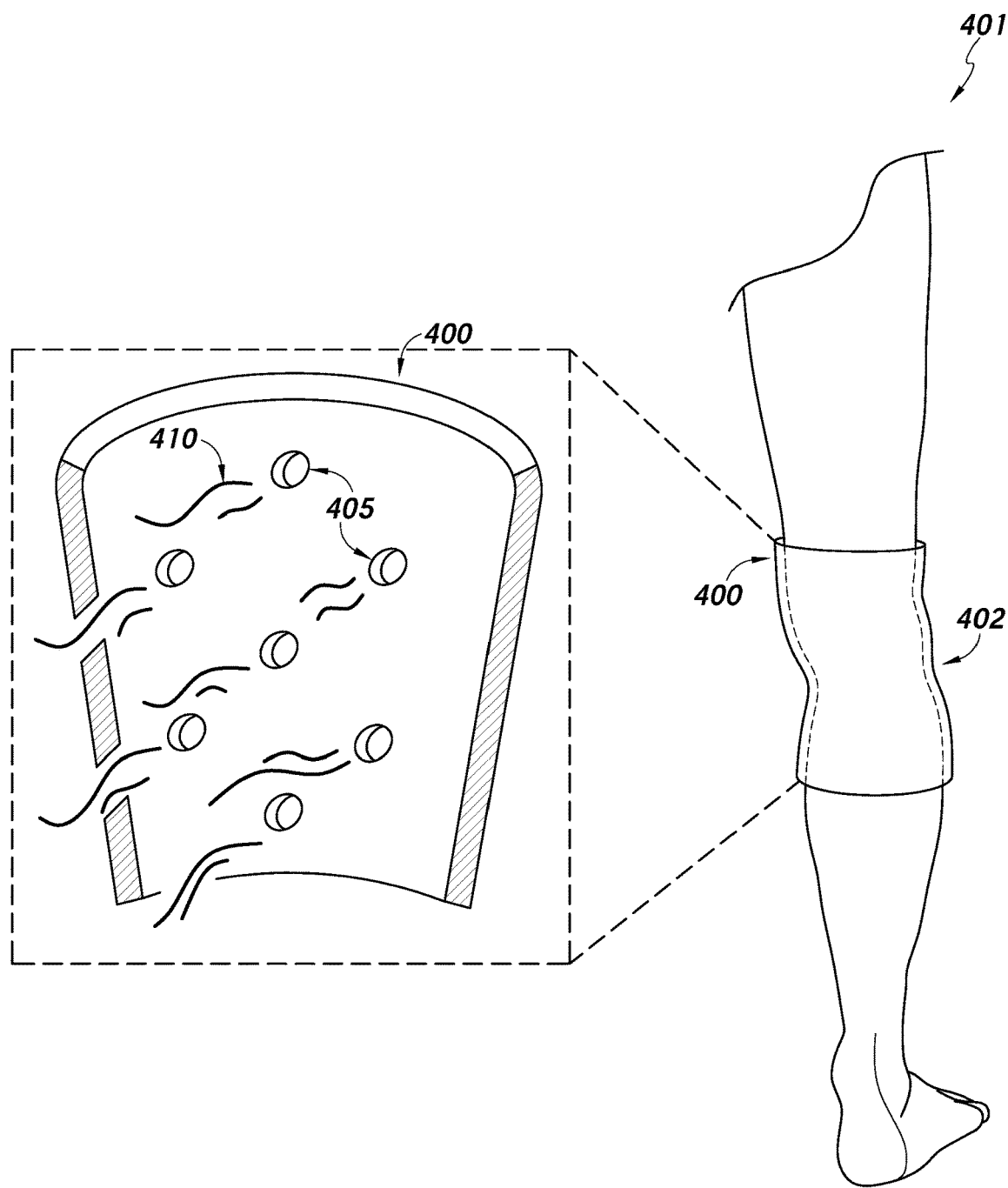
FIG. 4 provides a close-up view of at least a portion of a sleeve for providing heat and/or compression at or near a knee portion of a limb.

FIG. 4 provides a close-up view of at least a portion of a temperature management sleeve device/assembly 400 for providing heat and/or compression at or near a knee portion 402 of a leg/limb 401 of a patient. The sleeve 400 may be configured to provide warming through convective, conductive, and/or radiative heat transfer to the targeted area(s) of therapy. In some embodiments, the sleeve 400 is configured to provide compression functionality in addition to heating. The targeted area(s) may include, for example, a popliteal fossa area of the limb. The sleeve 400 may comprise one or more perforations 405 at least over an inner surface (e.g., a skin-interfacing surface) of the sleeve 400. The one or more perforations 405 may be configured to allow heated gas 410 to pass out of the sleeve 400 to in the direction of the patient's skin.

Figure 5:
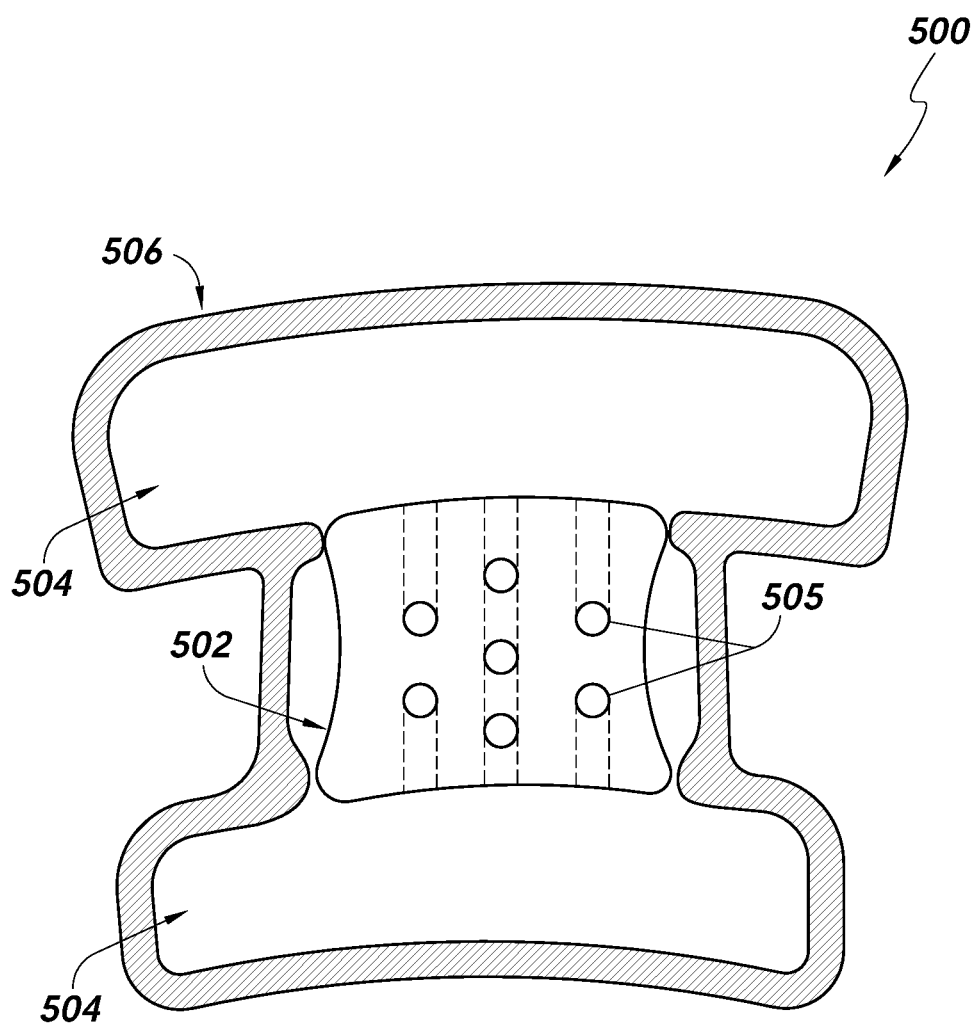
FIG. 5 illustrates at least a portion of a sleeve for providing heat and/or compression to at least one area of a patient's limb.

FIG. 5 illustrates at least a portion of a sleeve 500 for providing heat and/or compression to at least one area of a patient's limb. The sleeve 500 may comprise a warming portion/device 502 configured to hold heated gas and/or fluid. The terms "warming portion," "warming element," "warming bladder," "heating/heated bladder," "heating portion," and "heating element" are used herein to refer to any portion, device, and/or element of a sleeve configured to transfer/deliver heat to an area of a human body. The terms "warming" and "heating" are used herein in accordance with their broad and ordinary meanings and are used substantially interchangeably in some contexts herein. Heat may be delivered by the warming portion 502 convectively, conductively, and/or in any other suitable manner. In some embodiments, the sleeve 500 may further comprise one or more perforations 505 to allow heated gas and/or fluid to exit the sleeve and/or contact skin of the patient.

The sleeve 500 may further comprise one or more compression portions 504 configured to inflate with gas and/or fluid and/or to press against the patient's skin and/or compress the patient's limb. The terms "compression portion," "compression element," "bladder," "compression bladder," and "blood flow element" are used herein to refer to any portion and/or element of a sleeve configured to deliver compression to an area of a human body. The one or more compression portions 504 may be configured to inflate sequentially with, for example, warmed (or non-warmed) fluid to compress the limb and/or provide warming to the patient. In some embodiments, gas and/or fluid used to fill the warming portion 502 may also be used to fill the compression portions 504. However, the gas and/or fluid in the warming portion 502 may be separate and/or independent from any gas and/or fluid in the compression portions 504.

In some embodiments, the warming portion 502 and/or fluid channels within the warming portion 502 may have any of a variety of shapes, sizes, configurations, alignments, orientations, and the like. For example, the warming portion 502 and/or a fluid channel configured to carry heated fluid and/or gas within the warming portion 502 may have an at least partially coiled and/or spiraling structure. The partially coiled and/or spiraling structure may comprise one or more elements configured to allow bending, stretching, deformation, and/or other adjustments to the warming portion 502 to conform the warming portion 502 to a patient's limb surface. In some embodiments, the channel(s) may be configured to double-back one or more times in one or more generally straight vertical and/or horizontal paths.

The warming portion 502 and/or compression portion 504 may be configured to provide warming through conductive/radiative heat transfer to various targeted areas of therapy. In some embodiments, compression may be maintained during warming of the targeted area(s). Fluid and/or gas inflating and/or deflating the compression portions 504 within the sleeve 500 may be heated to provide warming to the limb. For example, the sleeve 500 may be configured to provide heating across the warming portion 502 and the compression portion(s) 504 while only the compression portions 504 may be configured to provide compression. In some embodiments, the sleeve 500 may comprise an adhesion portion 506 configured to attach and/or hold the sleeve 500 to the patient's limb (e.g., skin thereof). The adhesion portion 506 may comprise an outer portion of the sleeve 500 and/or may comprise and/or may be coated with any of a variety of adhesive materials.

Figure 6A:
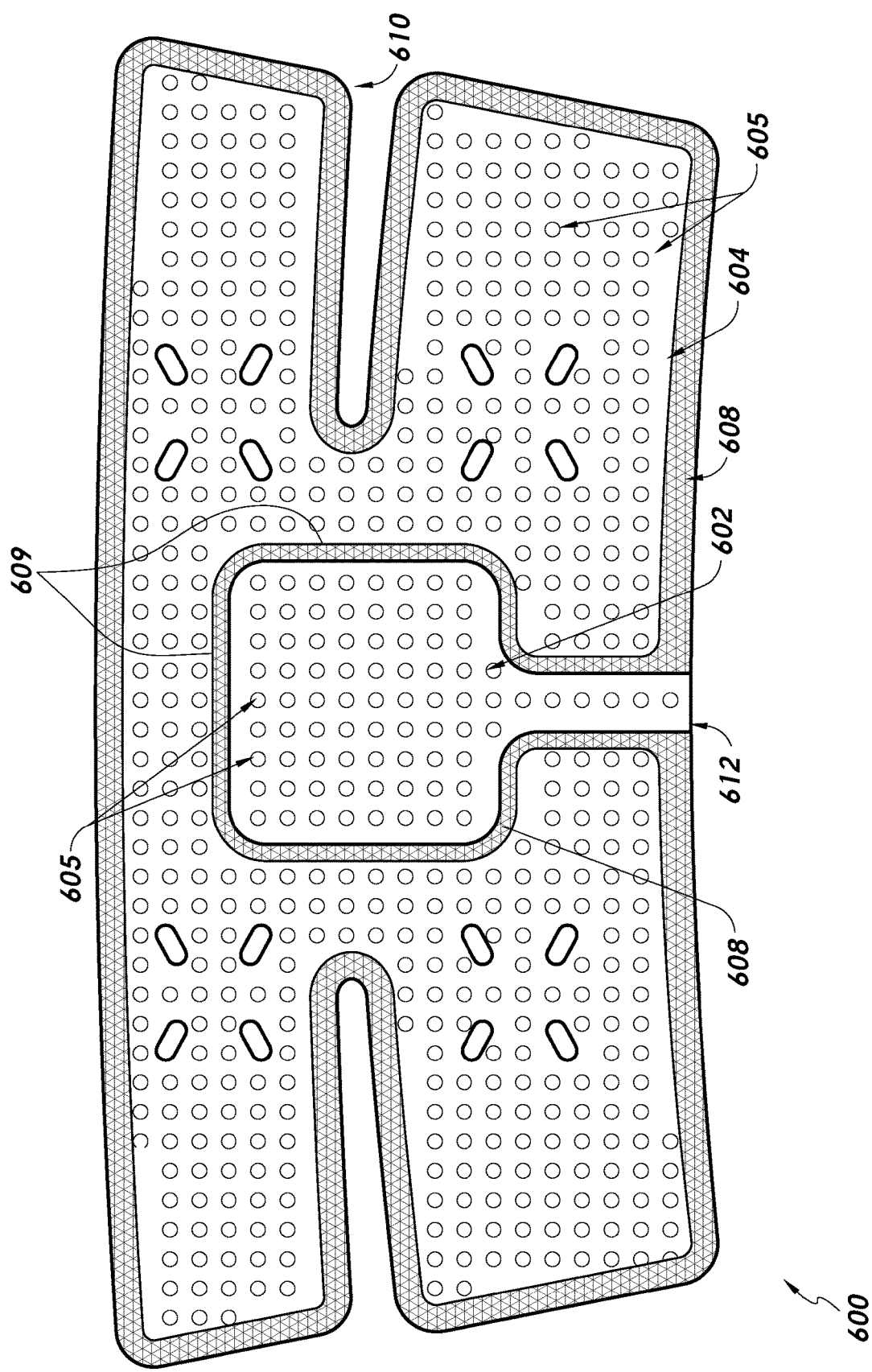
FIG. 6A illustrates an inner surface of at least a portion of a sleeve in accordance with some embodiments.

FIG. 6A illustrates an inner surface of at least a portion of a sleeve 600 in accordance with some embodiments of the present disclosure. The inner surface may comprise a warming portion 602 and/or a non-warming portion 604 (e.g., a compression portion). The warming portion 602 and/or non-warming portion 604 may be configured to contact and/or otherwise interface with a patient's skin. In some embodiments, the warming portion 602 and/or the non-warming portion 604 may comprise one or more perforations 605 configured to allow heated gas and/or fluid contained within, for example, the warming portion 602 (e.g., one or more fluid channels thereof) to pass out of the sleeve and into contact with the patient's skin. The non-warming portion 604 may not be configured to provide heat to the patient and/or may be configured to provide compression to the patient through tightening and securing of the strap portions 610 to one another. In some embodiments, one or both sides of the straps 610 include adhesive, Velcro, and/or other fastening features for fastening the straps over and/or around a limb of the patient.

In some embodiments, the warming portion 602 may be configured to provide heat to the patient via conductive, radiative, and/or convective heat transfer. For example, one or more wires, traces, and/or other conductive heating elements may be disposed within the warming portion 602, wherein such heating elements may be electrically powered using one or more wires electrically coupled thereto through an opening/channel 612 associated with the warming portion 602. When activated (e.g., when electrical current is passed therethrough), the conductive heating elements may heat-up, wherein such heat may radiate in the direction of the patient's skin and/or heat the material in contact/proximity with the patient's skin to thereby warm the patient's skin and surrounding tissue (e.g., at or near the popliteal fossa). In some embodiments, warmed gas and/or fluid may be passed through the warming portion 602 and out of the warming portion through perforations 605 therein to warm the patient's body (e.g., at or near the popliteal fossa). The warming portion 602 and/or non-warming portion 604 may comprise heating and/or compression bladders and/or foam or similar materials configured to contact the patient's skin.

The sleeve 600 may comprise closed-off borders 608 configured to surround the warming portion 602 and/or the non-warming portion 604. In some embodiments, the thickness of the sleeve at the borders 608 may be less than a thickness of the sleeve 600 at more central portions of the warming portion 602 and/or the non-warming portion 604. For example, the borders 608 may not comprise bladders and/or foam or similar materials. In some embodiments, the borders 608 do not generally contact the skin of the patient, at least with respect to certain portions of the borders 608, such as portions 609 that physically and/or fluidly isolate the warming portion 602 from the non-warming portion(s) 604. The borders 608 may represent gaps in the bladder(s) and/or foam or similar materials of the warming portion 602 and/or non-warming portion such that the borders 608 may allow the sleeve 600 to more easily be bent and/or otherwise shaped to fit a patient. The patterns of the borders 608 illustrated in FIGS. 6A and 6B are exemplary and other patterns of borders 608 and/or sizes and/or shapes of the warming portion 602 and/or non-warming portion 604 may be utilized.

The sleeve 600 may comprise one or more straps 610 configured to be wrapped around an area of the patient's limb. For example, the straps 610 may be configured to wrap around areas above and below the patient's knee, respectively, to allow the sleeve 600 to be secured such that the warming portion 602 is positioned at or near the popliteal fossa region of the patient's limb.

Figure 6B:
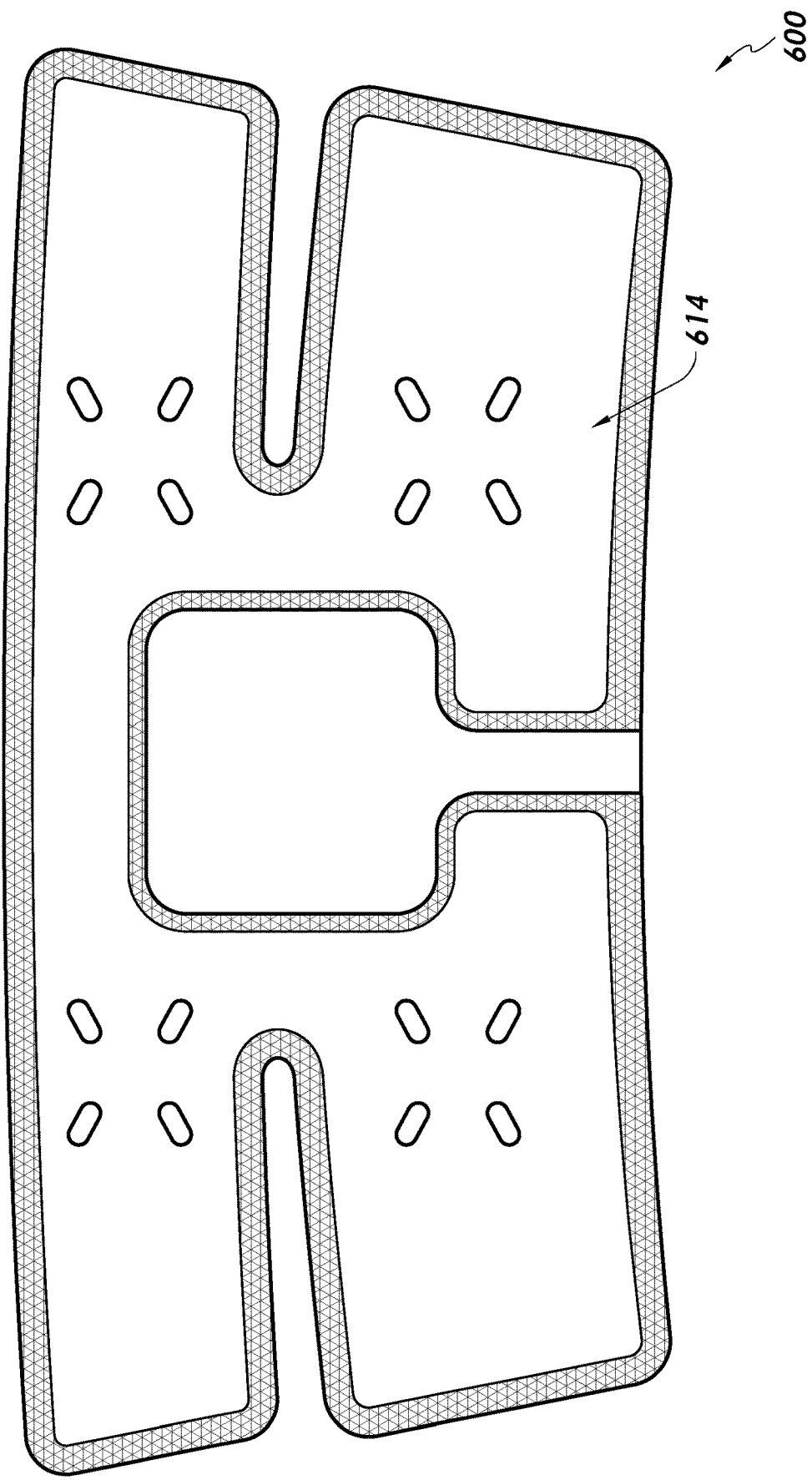
FIG. 6B illustrates an outer surface of at least a portion of a sleeve 600 in accordance with some embodiments.

FIG. 6B illustrates an outer surface 614 of at least a portion of a sleeve 600 in accordance with some embodiments. For example, the side of the sleeve 600 shown in FIG. 6B may generally be outward-facing when the sleeve is secured on the patient's limb. The outer surface 614 may comprise any of a variety of materials and/or may be configured to prevent heat from escaping. For example, one or more outer layers of the sleeve 600 may be disposed between any heating elements and/or compression and/or heating air chambers of the sleeve and the outside of the sleeve, wherein such layer(s) is/are fluid-tight. It should be understood that references herein to heat transfer through the use of gas as a heat transfer medium, or compression through the use of gas-filled bladders/chambers, any type of fluid may be used instead of, or in addition to, gas (e.g., air), including any suitable or desirable type of gas or liquid (e.g., water, such as heated water, or other liquid solution).

Figure 7:
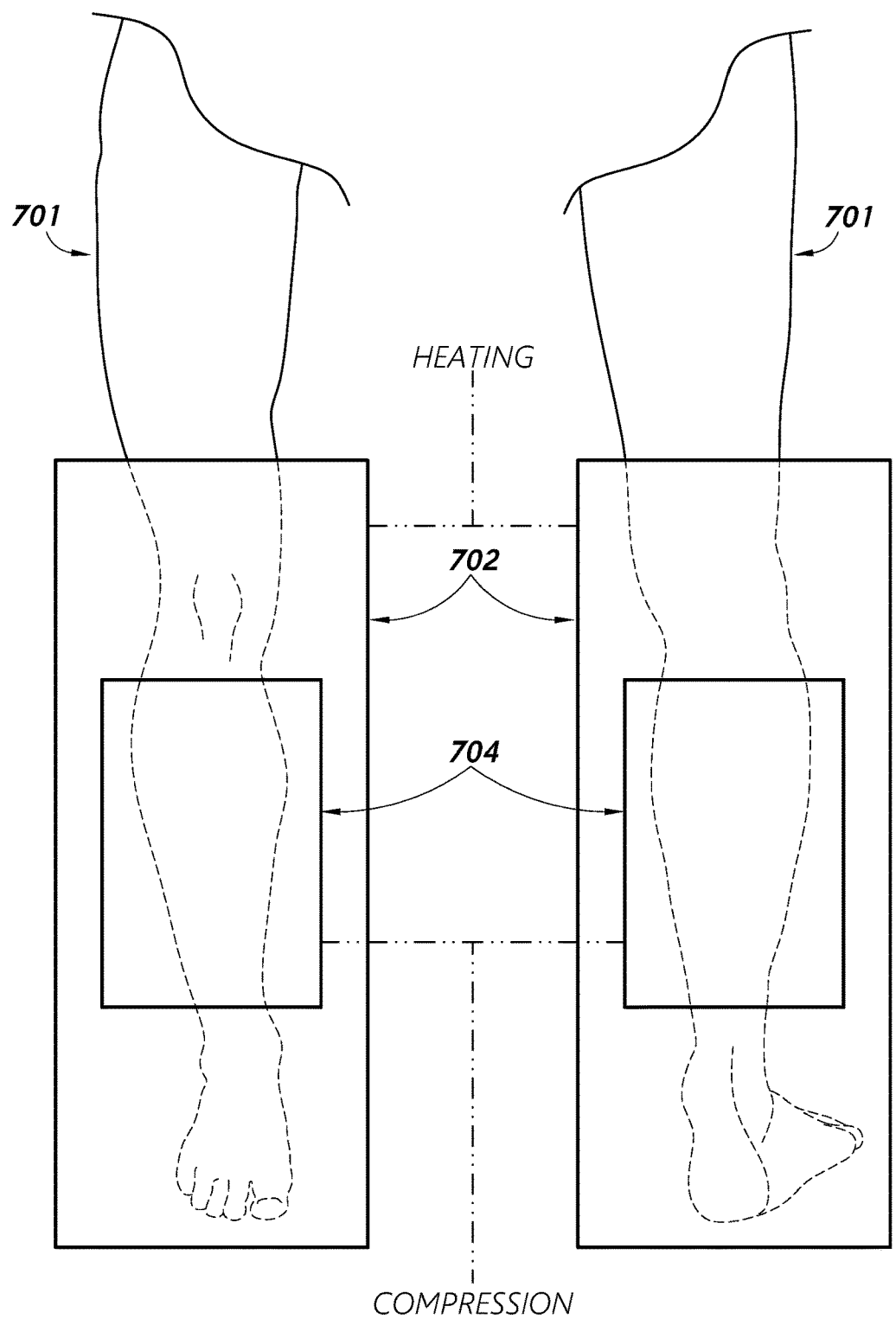
FIG. 7 provides a diagram illustrating heating and compression areas in accordance with one or more embodiments.

FIG. 7 provides a diagram illustrating general heating and compression areas of one or more sleeves described herein. In some embodiments, both heating therapy and blood flow (i.e., compression) therapy may be applied to the same areas of a patient's body. For example, as shown in FIG. 7, heating may be applied to a first area 702 covering a substantial portion of a patient's limb 701, including at least the knee and/or foot areas, while compression may be applied to a second area 704. For example, the first area 702 may include areas covering at least portions of the patient's foot, calf, knee (e.g., the popliteal fossa and/or knee cap), and/or thigh, while the second area 704 may include the calf.

Figure 8:
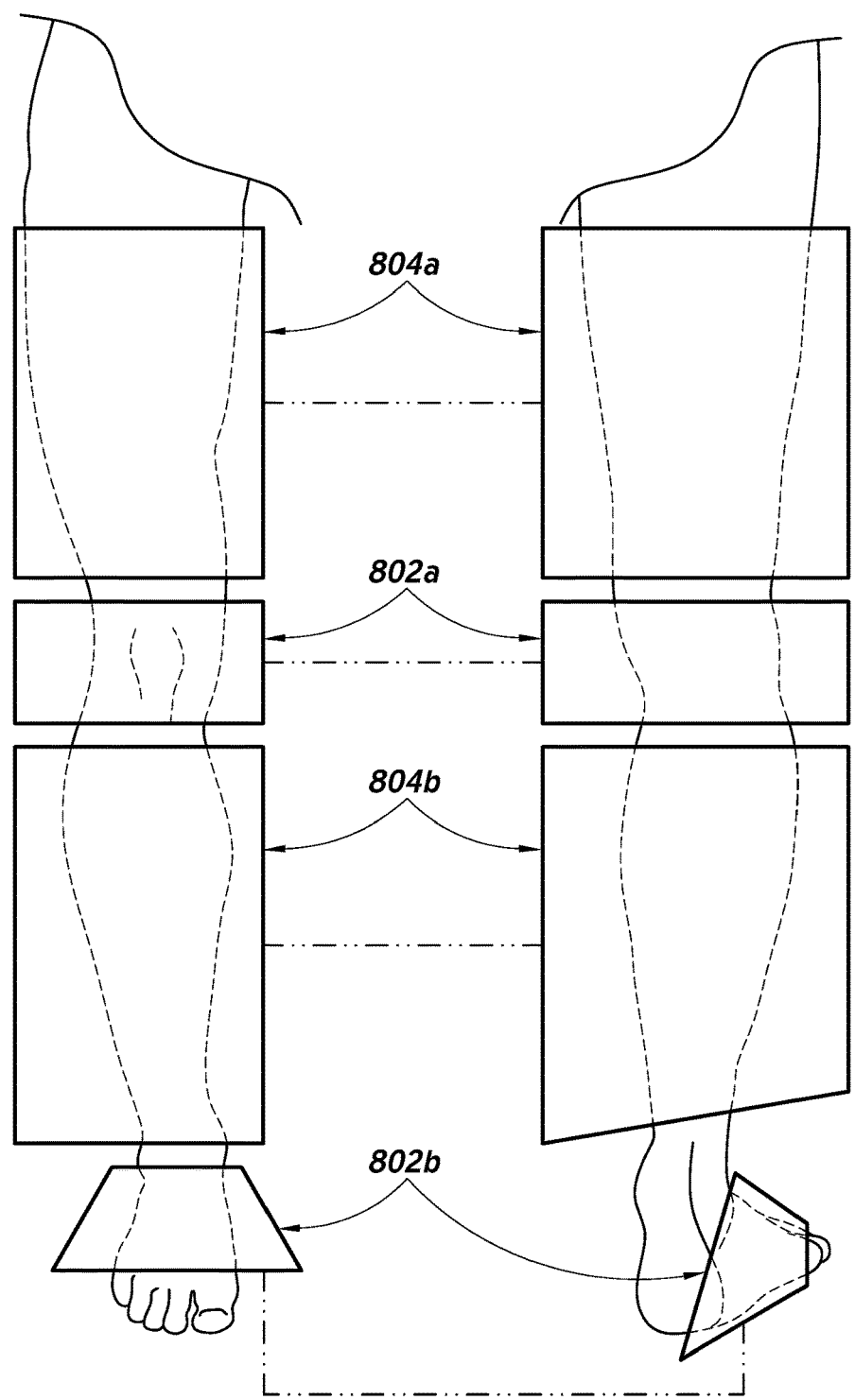
FIG. 8 provides another diagram illustrating heating and compression areas in accordance with one or more embodiments.

FIG. 8 provides another diagram illustrating heating and compression areas that may be associated with any of the embodiments of sleeves described herein. As shown in FIG. 8, in some embodiments, sleeves may deliver heat or compression to different areas of the patient's body. For example, heating may be provided to a first area 802*a* (e.g., at or around the patient's knee) and/or a second area 802*b* (e.g., a foot, such as at or around a sole of the patient's foot), while compression may be provided to a third area 804*a* (e.g., at or around the patient's thigh) and/or a fourth area 804*b* (e.g., at or around the patient's calf).

The inflation and/or deflation sequence of warming portions of sleeves in accordance with aspects of the present disclosure may be different from compression portions. For example, the warming portions (e.g., warming bladders, channels, and/or areas/compartments) may be configured to not completely deflate such that the warming portions maintain consistent skin contact. Moreover, the warming portions may be configured to maintain a lower maximum pressure compared to compression portions to avoid blood flow restriction. The warming portions may be configured to inflate and deflate at more rapid cycles than the compression portions to maintain a desired temperature profile at the desired heating location. In some embodiments, fluid providing compression and fluid providing warming may be separate fluids, may travel in distinct channels, and/or may remain isolated from each other within a sleeve.

Warming and Compression Elements/Mechanisms

Figure 9:
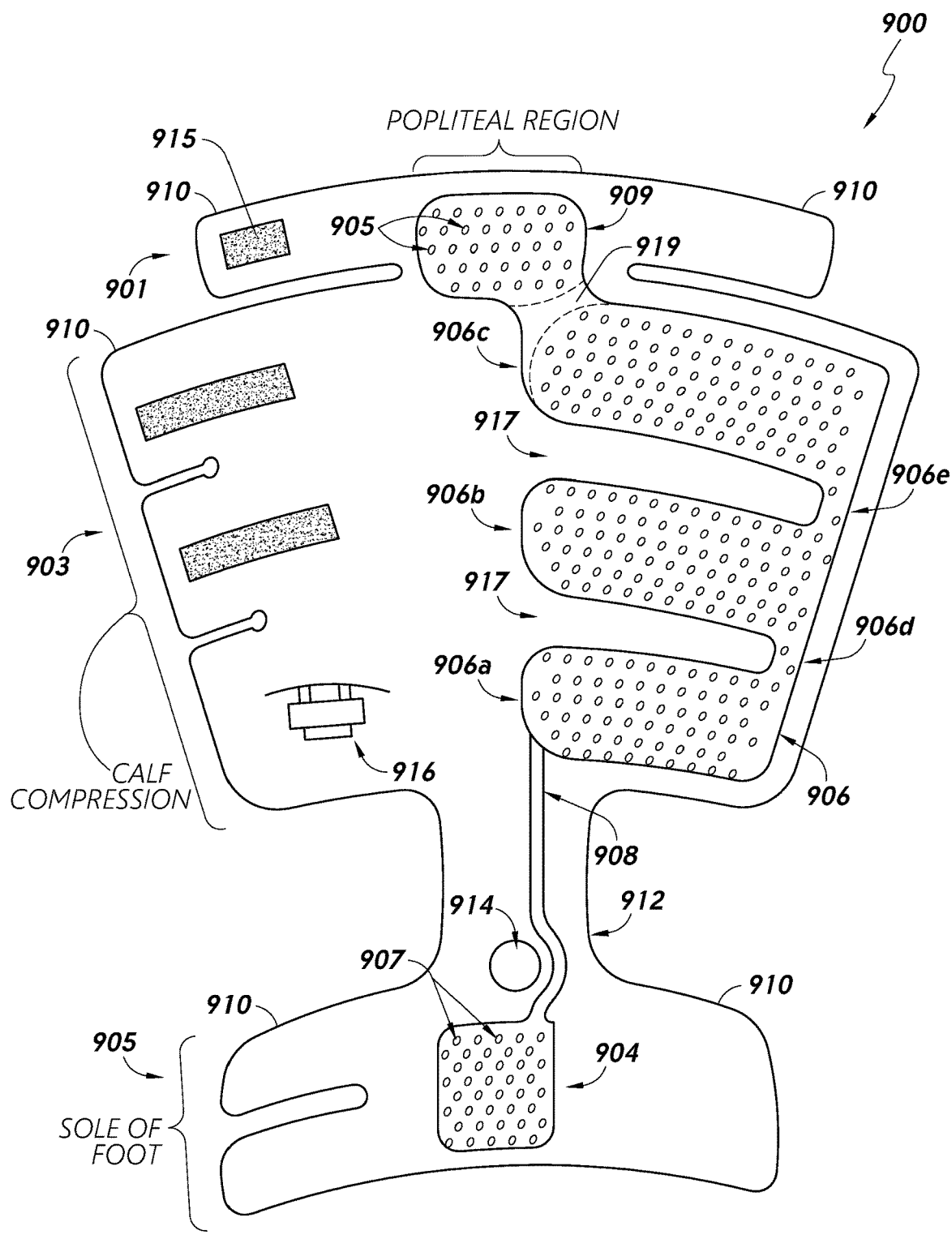
FIG. 9 provides a view of a sleeve configured to provide heating and/or compression via a first portion configured to contact a calf of a patient and a second portion configured to contact a sole of a foot of the patient in accordance with one or more embodiments.

FIG. 9 provides a view of a sleeve 900 configured to provide heating and/or compression via a first portion 901 configured to contact the back of a knee of a patient, a second portion 903 configured to contact a calf of a patient, and/or a third portion 905 configured to contact a foot of the patient. In some embodiments, the sleeve 900 may be configured to provide heat therapy using convective and/or other heating methods. The sleeve 900 may comprise one or more heating and/or compression bladders 906 which may be connected (e.g., in fluid communication) and/or may be separated (e.g., fluidly isolated) from each other. In some embodiments, one or more channels 908 may be configured to provide transport of fluid (e.g., gas) to one or more bladders 906, 904, 909 for delivering heating and/or compression. The one or more bladders 906 may comprise one or more perforations 905 positioned and configured to pass heated gas/fluid to targeted areas of the patient's body (e.g., the popliteal region and/or the sole of the foot). Although referenced using separate reference numbers, in some embodiments, two or more of the bladders 904, 906, 909 are in fluid communication with one another.

The sleeve 900 may comprise multiple portions configured to contact and/or provide heat and/or blood flow therapy to one or more areas of a patient's limb. For example, the sleeve 900 may comprise a first portion 901 configured to provide heat and/or compression to a patient's knee (e.g., at the popliteal fossa) and/or thigh, a second portion 903 configured to provide heat and/or compression to a patient's calf and/or surrounding areas, and/or a third portion 905 configured to provide heat and/or compression to a patient's foot (e.g., the sole of the foot) and/or the surrounding areas.

In some embodiments, channels 908 and/or bladders 906 for providing blood flow and/or compression therapy may not have perforations in at least one or more portions thereof. Bladders 906 for compression may utilize flowing gas for sequential compression. Bladders (e.g., 904 and/or 909) configured to provide heating may have perforations 907 and/or may be configured to provide a relatively continuous stream of heated gas/fluid for compression and/or heating therapy. In some embodiments, skin/tissue contact may be achieved without compression bladders 906. For example, one or more inserts (e.g., foam insert(s)) may be disposed in or on the sleeve 900 to press the bladders 906 and/or the perforations 905 against the patient's skin to establish and/or maintain surface contact between the sleeve 900 and the patient's skin at least in certain desired areas. The number and/or size of the perforations 905 can affect compression. For example, gas may escape more easily with a greater number and/or size of the perforations 905, thereby affecting the pressure within the sleeve 900.

With respect to the compression bladders 906, in some embodiments, some bladders 906 may not start filling until other bladders 906 reach a certain pressure. For example, fluid may be provided to the bladders 906 through the channel 908, initially passing into the lower/first bladder portion 906*a*. The first bladder portion 906*a* may be fluidly coupled to the second/intermediate bladder portion 906*b* via an interconnection channel 906d. In some embodiments, fluid may not propagate through the channel 906d into the second bladder portion 906b in substantial amounts until the fluid in the first bladder portion 906a reaches a certain pressure level due to the filling of the first bladder portion 906a. That is, the fluid entering the bladder 906a may sequentially fill the first bladder portion 906, then the second bladder portion 906b, and then the upper/third bladder portion 906c (via the interconnecting channel 906e). Although a certain amount of fluid may pass into the second 906b and third 906c bladder portions prior to the first bladder portion 906a reaching a maximum or threshold volume and/or pressure, the degree to which the first bladder portion 906a fills with fluid may be greater initially compared to the other bladder portion(s). Likewise, the second bladder portion 906b may fill to a greater degree and/or more quickly than the third bladder portion 906c prior to the second bladder portion 906b reaching a maximum or threshold volume and/or pressure. The heat-transfer fluid may further pass to the popliteal bladder portion 909. In some embodiments, the popliteal bladder or other type of heating element may be isolated from the bladder portions 906, such as by a break or barrier portion 919. The interconnection channels 906d, 906e may be sized/dimensioned to produce/control desired sequence/timing of sequential filling of the respective bladder portions 906.

In other embodiments, the first bladder portion 906a, second bladder portion 906b, and/or third bladder portion 906c may be independent of other bladder portions 906. For example, the first bladder portion 906a may not be connected to the second bladder portion 906b by a first interconnection channel 906d and/or the second bladder portion 906b may not be connected to the third bladder portion 906c by a second interconnection channel 906e. Moreover, in some embodiments, one or more bladders 906 may be pressure-controlled independently by an individual fluid channel 908. For example, the sleeve 900 may comprise multiple fluid channels 908 in which at least one of the multiple fluid channels 908 may provide pressure control to only one of the bladders 906.

In some embodiments, one or more bladders 906 may have various features to enable easier wrapping of the sleeve 900 around the patient's limb. For example, a bladder 906 may comprise dimples and/or other features. Furthermore, the bladders 906 may be separated by break portions 917.

In some embodiments, one or more channels 908 for delivering heated gas and/or fluid may not have perforations 905 and/or may act as bladders that may be configured to inflate/deflate with a single port. Gas can be cycled in and out of a heated bladder on a higher frequency than compression bladders 906. For example, if compression bladders 906 are cycled 1-2-3, heated bladders (e.g., 909, 904) may be cycled with each compression cycle 1-1-1. A cycle may have a duration of approximately sixty seconds but may be adjusted depending on an amount of heat dissipation. In some embodiments, the sleeve may comprise a single bladder 906 utilizing intermittent compression.

Compression may be controlled such that whenever heating is active, compression at target heating areas may be maintained. For example, compression at or near the popliteal fossa and/or the foot may be maintained during heating cycles to ensure that the generated heat is transferred to the popliteal fossa and/or foot. Compression bladders 906 may be filled with additional gas/fluid when pressure at the compression bladders 906 is detected below a threshold pressure value. In some embodiments, a foam pad may be utilized to establish and/or maintain surface contact between the heating bladders and the target areas.

Heating may be delivered via a sheet-type heating element/device, which may utilize either a convective or conductive configuration. Compression bladders 906 may be separate from the heating sheet. In some embodiments, the compression bladders 906 may be configured to maintain an ON state in which the compression bladders 906 continuously press inward in the direction of the skin of the patient. In some embodiments, one or more foam pads may be utilized in place of one or more compression bladders 906.

In some embodiments, heating may be delivered at least in part by fluid escaping and/or passing through perforations 905 of the sleeve 900, which may or may not be associated with the compression bladder portions 906 in addition to the heating portions 904, 909. In some embodiments, the sleeve 900 may comprise one or more straps 910 configured to be wrapped at least partially around a knee and/or other portion of a patient's limb. The arms 910 may be adjustable to allow for wrapping around patients of different sizes. For example, the straps 910 may include Velcro or other types of fastening features for fastening the straps 910 to one another around the patient's limb. Moreover, the length of the sleeve 900 may be adjusted (e.g., at a neck portion 912 between the second portion 903 and the third portion 905) by extending and/or tightening portions of the sleeve 900 and/or by folding and/or securing portions of the sleeve 900 onto and/or to other portions of the sleeve 900.

In some embodiments, the second portion 903 may be configured to provide heating and/or compression to the calf of the patient. A single supply or multiple supplies of heated or non-heated fluid may be used to provide heating to the various bladder portions 906 of the sleeve 900.

The sleeve 900 may comprise one or more features configured to enable easier application of the sleeve 900 to patients. For example, the sleeve 900 may comprise a heel locator 914 configured to be positioned at/over the patient's heel. The heel locator 914 may comprise an opening/cavity and/or visual marker in the sleeve 900. In some embodiments, the sleeve 900 may comprise an inlet and/or outlet port 916 configured to receive fluid, gas, and/or electricity from an external source (e.g., a controller) and/or have fluid drawn therefrom. As shown, the port 916 may be accessible outside of the sleeve to allow for engagement therewith using a corresponding connector associated with a fluid and/or electrical supply device.

Like other embodiments of devices described herein, the sleeve 900 may provide various advantages compared to certain alternative temperature management solutions, including ease of application and/or positioning of the devices on patients. Such devices may include various features (e.g., visual and/or physical indicators) for helping users avoid mistakes in application.

Figure 10:
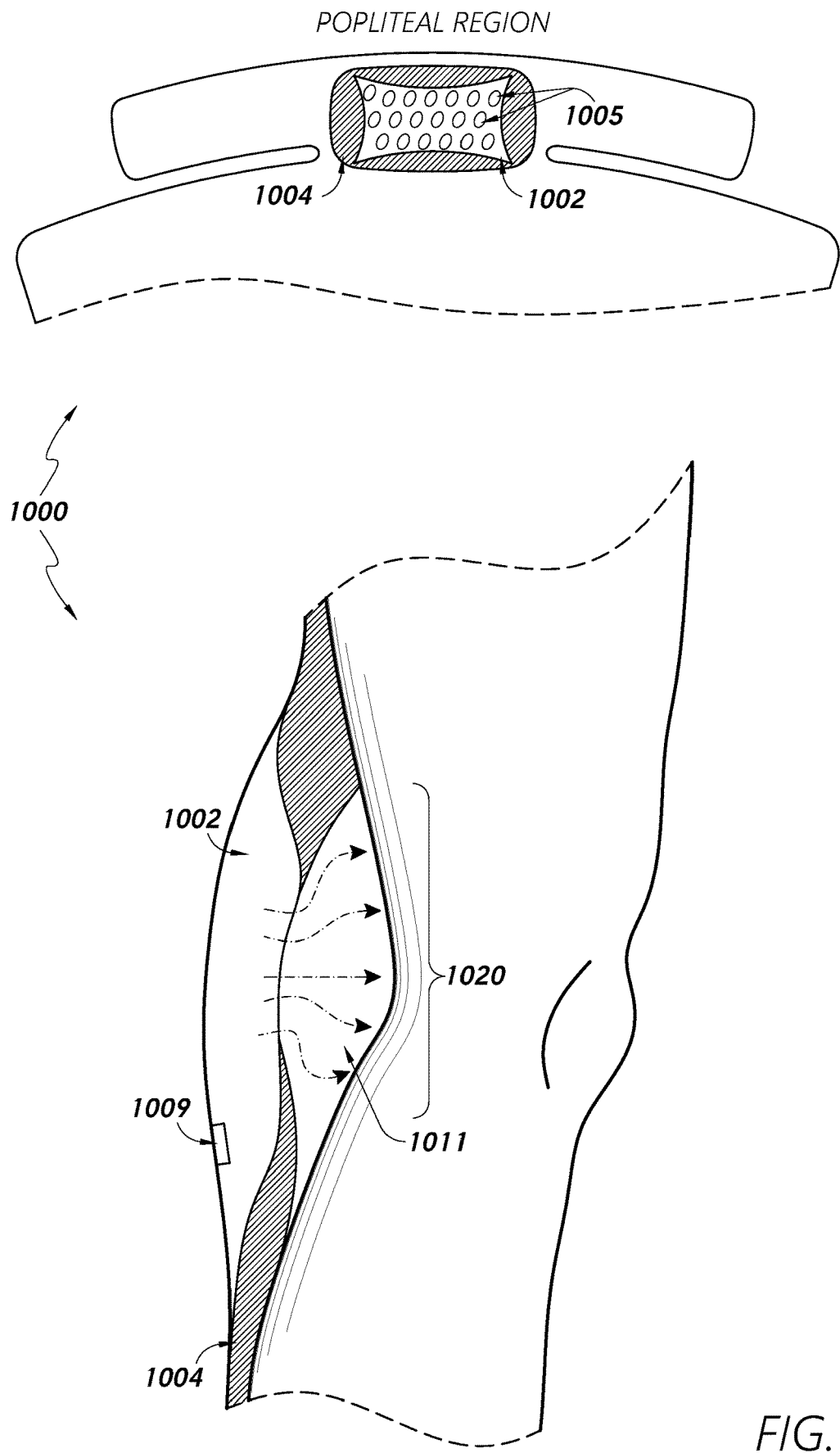
FIG. 10 provides multiple views of at least portions of a sleeve configured to provide heating and/or compression to areas of a patient's limb in accordance with one or more embodiments.

FIG. 10 provides multiple views of at least portions of a sleeve 1000 configured to provide heating and/or compression to areas of a patient's limb. The sleeve 1000 may comprise a warming portion 1002 configured to provide heat transfer to a target area of skin. The warming portion 1002 may comprise one or more perforations 1005 configured to allow heated gas to escape from the warming portion 1002 and contact/warm a patient's skin.

One or more supporting portions 1004 may be positioned adjacent to, near, and/or surrounding the warming portion 1002, as shown in FIG. 10. The supporting portions 1004 may be configured to be inflated with gas/fluid to provide contact with the patient's skin (e.g., at the tissue surrounding the popliteal fossa) and/or to form an unoccluded region 1011 (i.e., cavity or empty space) between the warming portion 1002 and the patient's skin (e.g., at the popliteal fossa 1020). In this way, the unoccluded region 1011 between the warming portion 1002 and the patient's skin may be filled with heated fluid. In some embodiments, the supporting portions 1004 may be configured to at least partially overlap with the warming portion 1002 to be situated between at least a portion of the warming portion 1002 and at least a portion of the patient's skin. In this way, the supporting portions 1004 may be configured to more effectively create separation between the warming portion 1002 and the patient's skin so that the warming portion 1002 does not burn the patient's skin.

The supporting portions 1004 may comprise inflatable bladders around the warming portions 1002 and/or may be configured to provide an adequate distance of the sleeve 1000 away from the skin so to avoid occlusion of the perforations 1005 of the warming portion 1002. The supporting portions 1004 may be configured to be inflated to a pressure that is sufficient to provide spacing for convective heat transfer without undesirably limiting blood flow. For example, the supporting portions 1004 may be inflated to a pressure that is less than an inflation pressure of a compression portion of the sleeve 1000 (e.g., configured to compress the patient's calf areas; not shown in FIG. 10).

In some embodiments, the warming portion 1002 may comprise at least one temperature sensor 1009. In some embodiments, the sensor 1009 may be configured to be positioned at or near the geometric center of the warming portion 1002 to measure the temperature of the warming portion 1002 and/or the heated skin. As with any of the embodiments disclosed herein, in some embodiments, the sleeve 1000 may comprise two or more temperature sensors (e.g., thermistors), which configured to measure the temperature of both the warming portion 1002 and the heated skin simultaneously. Multiple temperature sensors (e.g., thermistors) may be placed along the edges of the warming portion 1002 to measure the temperature gradient across the warming portion 1002 and respective contacting skin region. In some embodiments, the thermistors may be embedded directly into the warming portion 1002. Temperature sensors may be utilized to help regulate the temperature of the warming portion 1002 below a maximum temperature and/or above a minimum temperature. In some embodiments, the temperature of the warming portion 1002 may be maintained such that the temperature remains within a temperature range and/or oscillates between a maximum and minimum temperature at a predetermined period or frequency.

The supporting portions 1004 may not comprise perforations 1005 as the supporting portions 1004 may not be configured to deliver heat. The warming portions 1002 and/or the supporting portions 1004 may be configured to be filled with heated and/or unheated gas. As the heated gas fills the unoccluded region 1011, the heated gas may hold the unoccluded region 1011 open and/or may maintain separation between the warming portion 1002 and the patient's skin.

Figure 11:
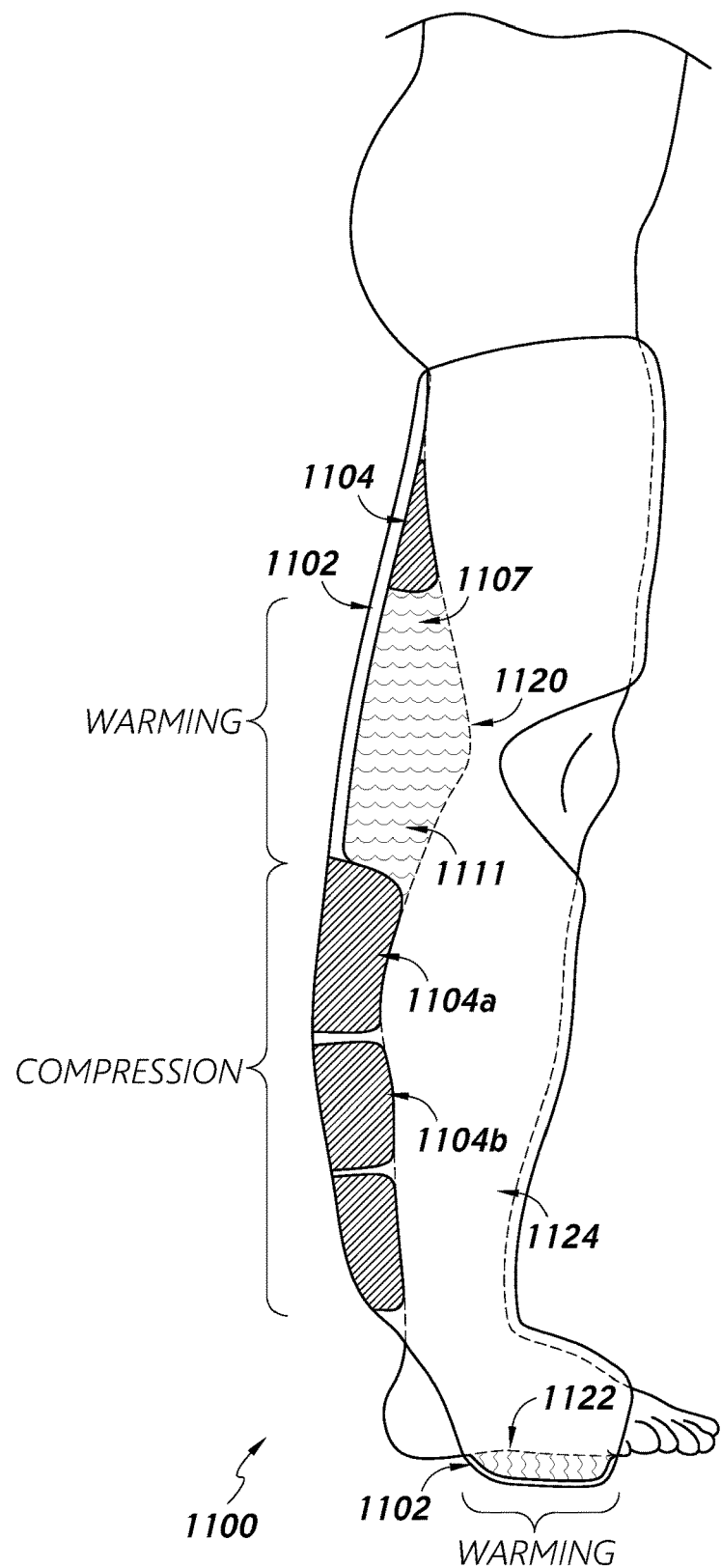
FIG. 11 provides a side view of a sleeve configured to provide heating and compression to a patient's limbs in accordance with one or more embodiments.

FIG. 11 provides a side view of a sleeve 1100 configured to provide heating and compression to a limb of a patient. The sleeve 1100 comprises warming portions 1102 configured to deliver heated gas/fluid 1107 to target areas (e.g., the popliteal fossa 1120 and/or the sole of the foot 1122) of the patient's limb 1101. The sleeve 1100 may further comprise one or more compression portions 1104 configured to create separation between the warming portions 1102 and the patient's skin and/or to provide compression therapy to targeted areas (e.g., the calf area 1124) of the patient's limb.

In some embodiments, different compression portions 1104 may be configured to have different pressure levels. For example, a first compression portion 1104a near a warming portion 1102 may be configured to have a lower pressure than a second compression portion 1104b. In this way, the first compression portion 1104a may be configured to effectively create and/or maintain an unoccluded region 1111 between the warming portion 1102 and the patient's skin without substantially restricting blood flow, while the second compression portion 1104b may be configured to provide compression therapy to the targeted areas.

Figure 12:
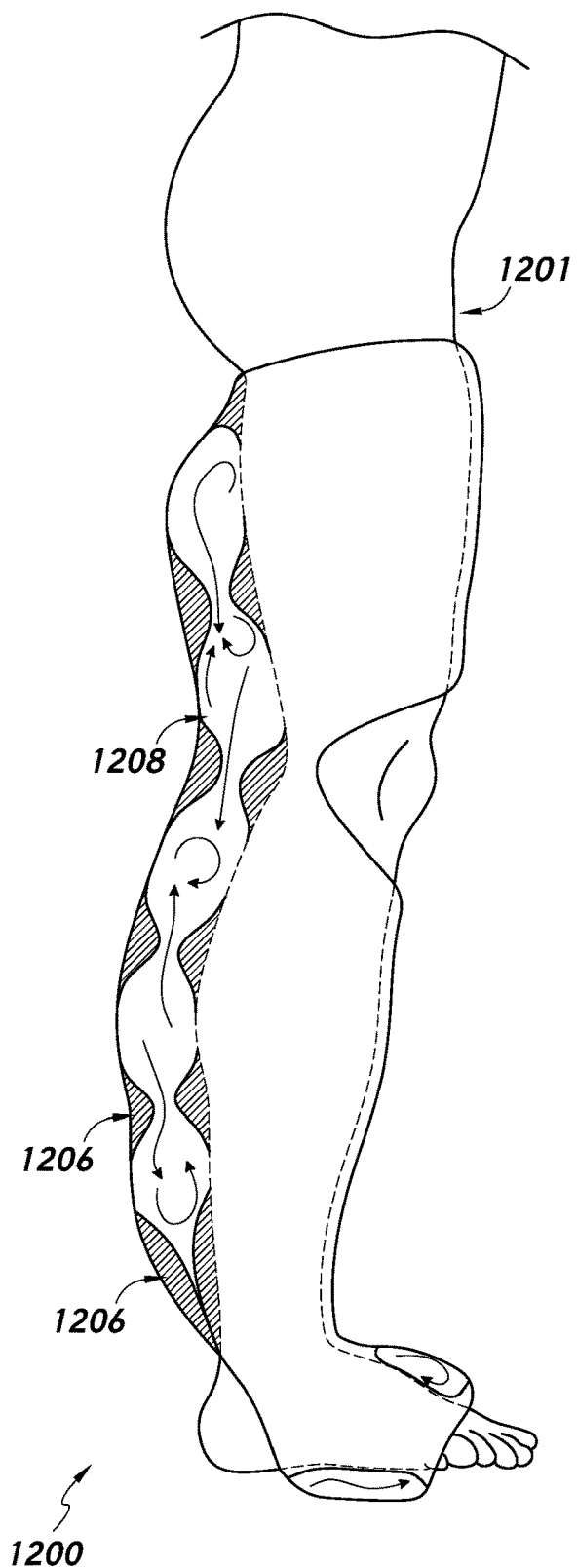
FIG. 12 provides a side view of a sleeve configured to provide convective heating and/or compression to a limb of a patient in accordance with one or more embodiments.

FIG. 12 provides a side view of a sleeve 1200 configured to provide convective heating and/or compression to a limb 1201 of a patient. The sleeve 1200 may comprise one or more bladders 1206 configured to be inflated with gas and/or fluid. The sleeve 1200 may further comprise one or more fluid chambers or channels 1208 configured to carry heating and/or compression fluids/gases. For example, the one or more chambers 1208 may be configured to fill with heated fluid to deliver warming therapy to various areas of the patient's limb 1201. In some embodiments, the gas and/or fluid passing through the one or more chambers 1208 may be configured to deliver compression to various areas of the limb 1201. In the example shown in FIG. 12, the sleeve 1200 may comprise a single fluidly-connected chamber/channel 1208. However, the sleeve 1200 may comprise any number of chambers 1208. The flow of the heated fluid through the channel(s)/chamber(s) 1208 can improve the heat transfer characteristics of the sleeve through convective effects of the moving fluid.

Figure 13:
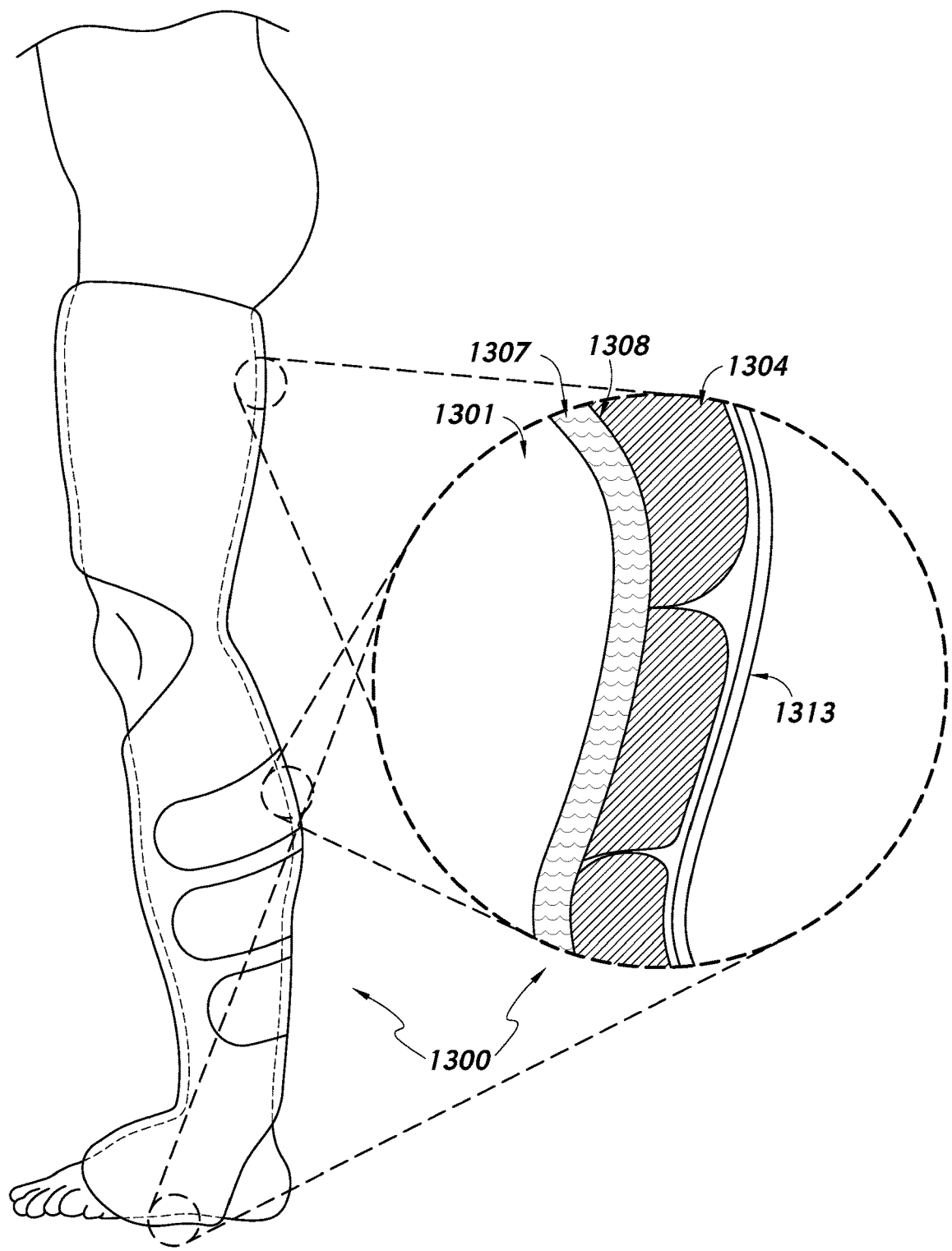
FIG. 13 provides a close-up view of a sleeve configured to provide heating and/or compression to one or more areas of a patient's limb in accordance with one or more embodiments.

FIG. 13 provides a close-up view of certain portion(s) of a sleeve 1300 configured to provide heating and/or compression to one or more areas of a patient's limb. In some embodiments, the sleeve 1300 may be configured to apply warming throughout some or substantially all of the patient-contacting portions of the sleeve 1300 that are associated with heating element(s) 1307. In some embodiments, the warming may be generated through the same material that houses the compression elements or through a separate layer disposed at least in part between the compression element(s) and the patient's skin (i.e., internal to the compression element(s)). For example, one or more compression elements 1304 may be configured to be inflated with heated gas and/or fluid, which may cause heated gas 1307 to fill a chamber 1308 in contact with the patient's skin 1301 and/or adjacent to the one or more compression elements 1304. In some embodiments, the heating element/chamber 1308 may be at least partially composed of one or more thermoelectric or resistive-heating pads or devices. In some embodiments, the heating element/chamber 1308 may be patterned and/or configured to allow for desirable physical deformation during compression, such as to accommodate certain anatomical features. In some embodiments, the heating element/chamber 1308 and/or other warming portions may be independent of the compression elements 1304, wherein the element/chamber 1308 may be applied directly to the patient prior to the placement of the compression elements 1304 to the respective limb. The elements/chambers 1308 may be configured to provide heating using one or more of electrical resistance, exothermic chemical reaction, ultrasound, and radiation. The element/chamber 1308 may be directly affixed to the patient using one or more of adhesives, retention members, and electromagnetic forces.

The compression elements 1304 and/or an outer layer 1313 of the sleeve 1300 may at least partially overlap and/or cover the heating element/chamber 1308 to enhance the effectiveness of heat transfer from the element/chamber 1308 to the desired anatomical region (e.g., the popliteal fossa and/or sole of the foot). In some embodiments, the use of a compressible material at the compression elements 1304 posterior (i.e., behind) to the chamber 1308 may improve skin contact and help provide an even distribution of warming. The compressible material may be immediately behind/external-to the chamber 1308 and internal to the outer layer 1313 where various sleeve fixation elements may be located. The material thickness of at least some portions of the sleeve 1300 may be, for example, between 5 mm and 15 mm but can range from 1 mm to 40 mm, or thicker.

In some embodiments, single or multiple compression elements 1304 (e.g., bladders) may be positioned behind/posteriorly-to the heating element/chamber 1308 to enhance skin contact of the heating element/chamber 1308. The compression element(s) 1304 may be configured to remain perpetually in an inflated state and/or may be inflatable at fixed or varying intervals and/or for fixed or varying durations. In some embodiments, a compression element(s) 1304 may have a non-uniform shape to accommodate the anatomy of the heating element/chamber 1308. The use of an adhesive substance on the internal surface of the element/chamber 1308 may be applied to enhance the efficacy of heat contact to the anatomical location. In some embodiments, the sleeve 1300 may comprise a heating element pattern, form, or material that may remain sufficiently biased towards the anatomy of a patient without the assistance of additional biasing members.

In some embodiments, the heating element/chamber 1308 may be configured to stretch and/or the outer layer 1313 may be configured to stretch or not to stretch. The compression elements 1304 may be configured to press the heating element/chamber 1308 against the skin 1301 to create and/or maintain surface contact between the skin 1301 and the chamber 1308 and/or the compression elements 1304 may be configured to induce circulation and/or increase flow of blood in the patient's limb. In some embodiments, the compression elements 1304 may be configured to be intermittently inflated and deflated to create intermittent contact between the element/chamber 1308 and the skin 1301.

Figure 14:
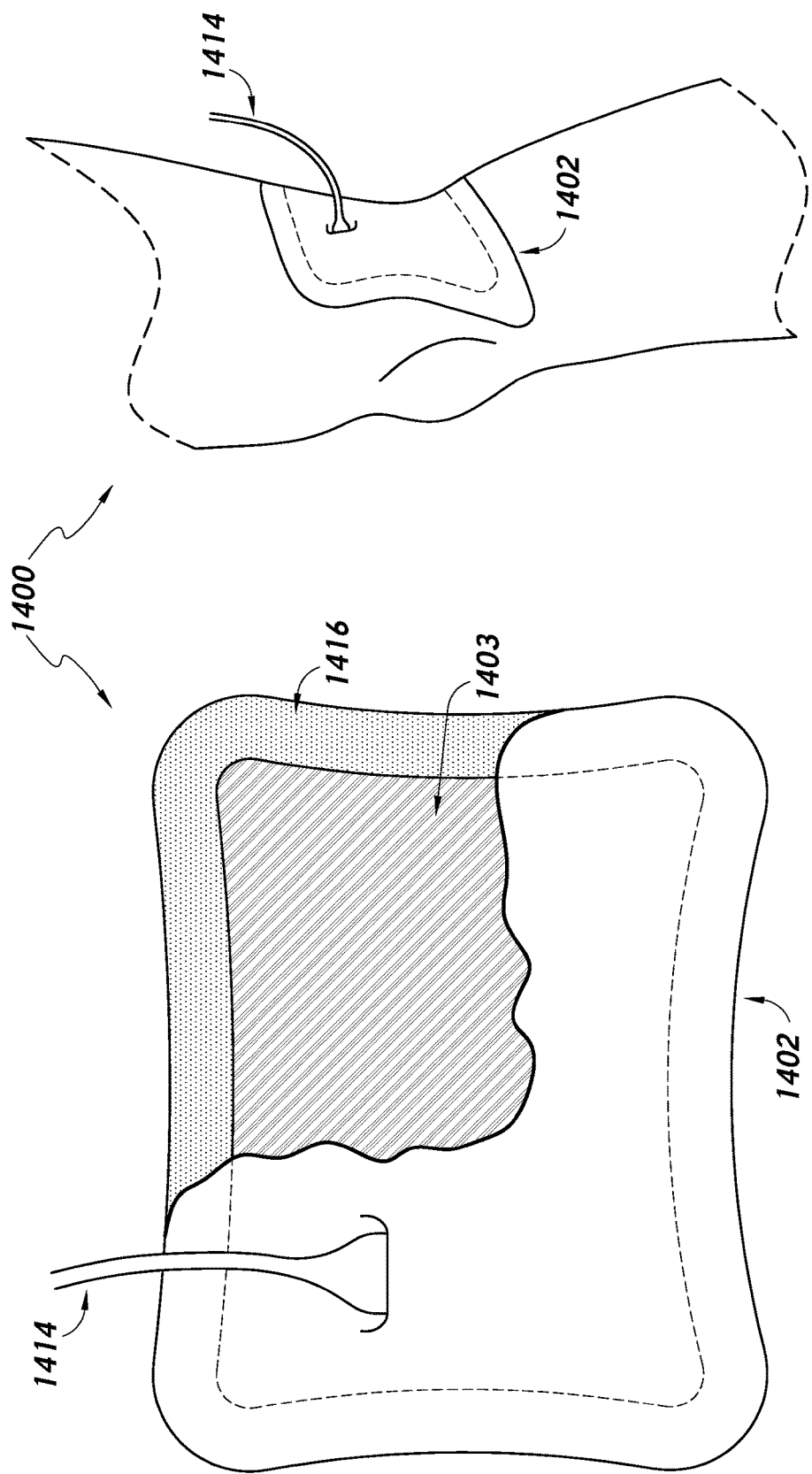
FIG. 14 provides an illustration of at least a portion of a sleeve for maintaining or increasing the body temperature of a patient in accordance with one or more embodiments.

FIG. 14 provides a cutaway view of at least a portion of a temperature management sleeve or patch device 1400 for maintaining or increasing core body temperature of a patient. In some embodiments, the sleeve/patch 1400 may include an electrical connection interface channel/connector 1414 configured to be connected between a heating element 1402 and an energy source for the heating element 1402. The electrical connection 1414 to the heating element 1402 may be configured to be biased medially or laterally along an edge of the heating element. In some embodiments, a sleeve/patch 1400 configured for providing heat to a sole of a foot may include the electrical connector 1414 proximally located along a vertical edge and distally biased so to lay flat on the patient bed during use. The electrical connector 1414 may be disposed/positioned in a laterally offset position, as shown, so as to remain free from the posterior region of the limb, for example, the sole of the foot or the popliteal fossa. In some embodiments, the electrical connector 1414 may include a stress-relief feature just proximal to the electrical connector 1414. The stress-relief feature and electrical connector 1414 may be further configured to maintain a hermetic seal, which may be achieved through mechanical interference, one or more O-rings, gaskets, adhesives, sealants, grease, and plugs, or the like.

In some embodiments, the sleeve/patch 1400 may comprise an adhesive 1416 around an outer border of the heating element. In some embodiments, the adhesive portion 1416 may be configured to seal the sleeve/patch 1400 to an area of skin of the patient. In some areas, the adhesive portion 1416 may be configured to overlap with a warming region 1403 of the sleeve/patch 1400. The adhesive 1416 may comprise hydrogel and/or other suitable substance. In some embodiments, the adhesive 1416 may be at least partially thermally conductive. In optional embodiments, the adhesive 1416 may be heated and/or may be used as a heating element in the warming region 1403.

The electrical connector 1414 may be configured to be coupled to an interface of one or more compression bladders and/or fluid transferring members. For example, the electrical connector 1414 may be coupled to fluid tubing and/or electrical wire(s)/trace(s). In some embodiments, the electrical connector 1414 may comprise at least one fluid-transferring channel, at least one heating energy (e.g., electrical energy) channel, at least one sensor feedback transmission line, and/or at least one ground interface, wherein the electrical connector may be configured to maintain hermetic seals to each other and/or to the external environment. Furthermore, the heating, sensor, and ground channels/interfaces of the multi-channel electrical connector 1414 may be configured to provide electrical connectivity achieved through electrical connector(s) to either a device controller at one end and a connecting cable at the other, or a connecting cable at one end and a device sleeve/patch on at other, or a device controller at one end and a device sleeve/patch at the other. In some embodiments, the sleeve/patch 1400 may comprise at least one multi-channel connector configured to support at least one compression element, at least one heating element 1402, and/or at least one temperature sensor. The sleeve/patch 1400 may be configured to be connected to more than one device controller through more than one electrical connector 1414. Each controller may be configured to deliver the same modalities (compression and/or heating) or different modalities.

Ease-of-Use Features of Limb Sleeve Devices

In some embodiments, the sleeves described herein may be configured to fit into an existing hospital workflow. For example, a sleeve device may be configured to functionally drive sequential compression and/or provide heat to various target areas of a patient (e.g., the sole of the foot and/or the popliteal fossa). In some embodiments, the sleeve may allow for at least limited patient mobility (e.g., a patient may walk around while wearing the sleeve). One or more sleeves may be configured to provide a universal fit (e.g., no left-/right-bias). Some sleeves may be configured for single-use and/or multi-use. Moreover, the approximate operating life of a sleeve may be at least eight hours.

Figure 15:
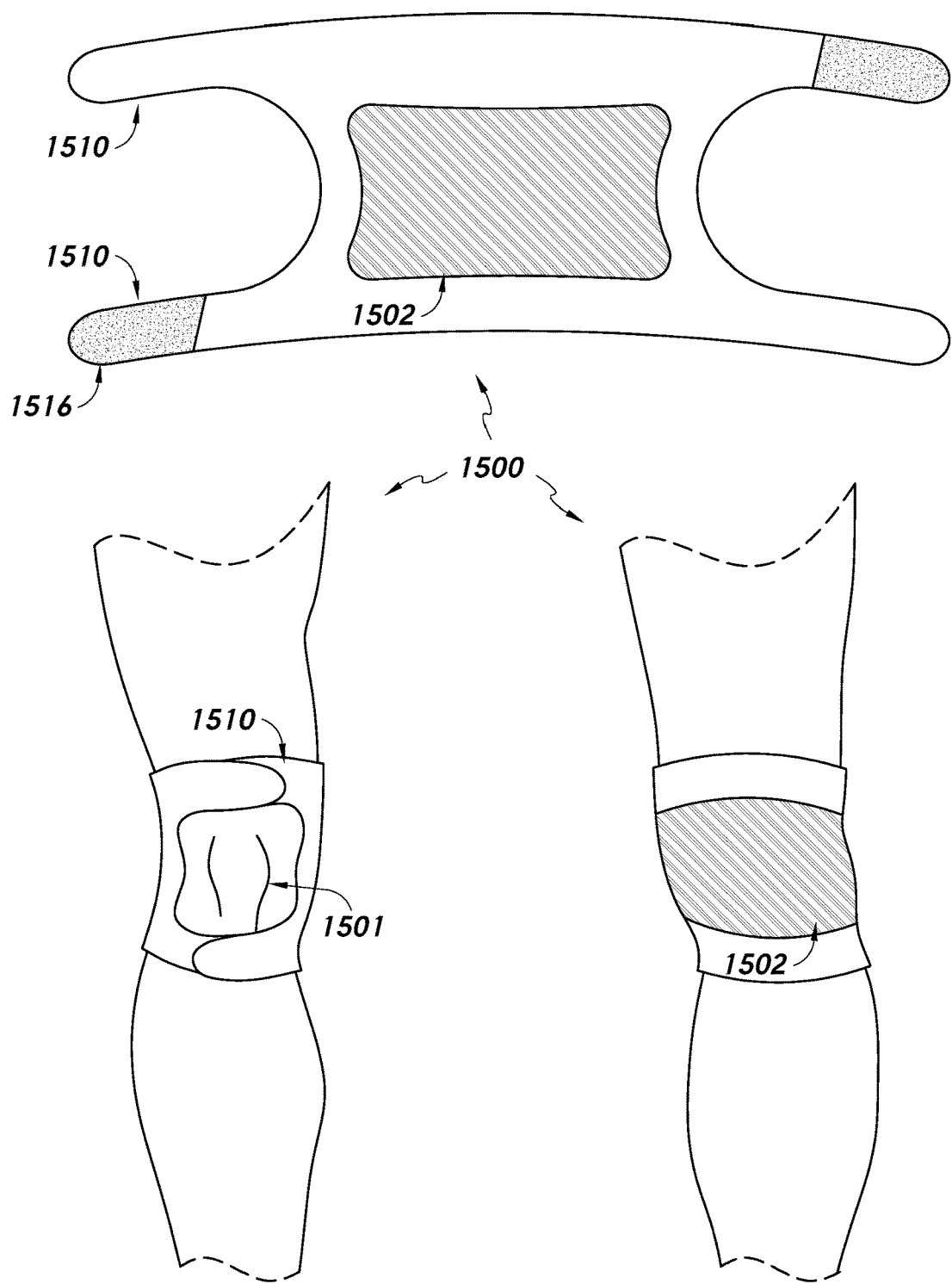
FIG. 15 provides views of a sleeve configured to provide improved ease-of-use in accordance with one or more embodiments.

FIG. 15 provides views of at least a portion of a sleeve 1500 configured to provide improved ease-of-use. In some embodiments, the sleeve 1500 may comprise a warming portion 1502 configured to deliver heat to a target area (e.g., the popliteal fossa) when the sleeve 1500 is placed over a patient's knee and/or other body part(s). The sleeve 1500 may also comprise one or more straps 1510, some of which may comprise a attachment/fastening feature 1516 (e.g., Velcro, adhesive, clip(s), hook(s), or the like) to allow the sleeve 1500 to be adhered to skin of a patient and/or to other portions of the sleeve 1500 (e.g., at the strap(s) 1510).

The sleeve 1500 may comprise various decals, icons, and/or other visual indicators indicating proper orientation of the sleeve 1500, such as at desired area(s) of a patient's limb. In some embodiments, the sleeve 1500 may be configured such that the straps 1510 surround the kneecap 1501 of the patient, as shown. For sleeves 1500 configured for application at/on a foot of a patient, the sleeve 1500 may comprise a heel locator, for example.

In some embodiments, the warming portion 1502 may be configured to be placed against the skin of the patient, whether or not the warming element associated therewith is covered by one or more layers of material/fabric or not. The warming portion 1502 may comprise a compressible foam pad and/or other materials configured to maintain constant surface contact and/or pressure of the sleeve 1500 and/or warming portion 1502 against the skin. In alternative embodiments, the sleeve 1500 may comprise one or more compression bladders. Such compression bladder(s) may not be intermittently pumped and/or may be fully inflated for the duration of the operation.

The sleeve 1500 may comprise an elastic material such that the sleeve 1500 may be configured to stretch to maintain surface contact and/or pressure at the skin. Such elasticity may present a substantially constant force against one or more areas of the skin when the sleeve 1500 is configured on the patient's limb. In some embodiments, the sleeve 1500 may comprise one or more elastic strips welded or otherwise attached/coupled to the sleeve 1500. The straps 1510 of the sleeve 1500 may be configured to be position at various angles and/or tensions to change the stretch and/or compression point from an edge of the warming portion 1502 to a center position of the sleeve 1500.

In some embodiments, the sleeve 1500 may comprise a compression element configured to be situated at a top portion of a calf muscle of the patient. A compression element may comprise an assembly consisting of multiple welded/coupled compression bladders. Each compression bladder may be configured to be connected to an independent channel of the sleeve connector and/or gas/fluid may be pumped into and/or out of the bladders to create compression on the encapsulated/proximate limb portion. In some embodiments, compression bladders may have "dimpled" elements (e.g., periodic holes welded, pressed, and/or cut in the bladder) to improve compression uniformity around the target limb portion. For example, the compression element may be a pre-assembled part that may be integrated into the sleeve 1500 in the final assembly.

FIG. 16 provides side views of an inflatable sleeve 1600 in a deflated state 1600a and in an inflated state 1600b. The sleeve 1600 may comprise a warming portion 1602 configured to contact a patient's skin and/or deliver heated gas to the patient's skin. In some embodiments, the sleeve 1600 may comprise a compression portion 1604 configured to be inflated with gas/fluid. The gas/fluid may be heated to provide warming functionality as described herein.

In the deflated state 1600a, a curvature of the popliteal fossa 1601 region of the patient's knee area may create a gap 1609 between the warming portion 1602 and the skin of the patient and/or may otherwise prevent the warming portion 1602 of the sleeve form contacting the skin in a uniform manner. However, when the compression portion 1604 is inflated in the inflated state 1600b, the compression portion 1604 may be configured to press the warming portion 1602 to create and/or maintain contact between the warming portion 1602 and the skin 1601 at the popliteal fossa. The warming portion 1602 may include any type of heating element(s), including one or more heating pads (e.g., comprising one or more resistive heating conductors), heated-fluid channels, chemical heating materials, and/or the like.

Figure 17:
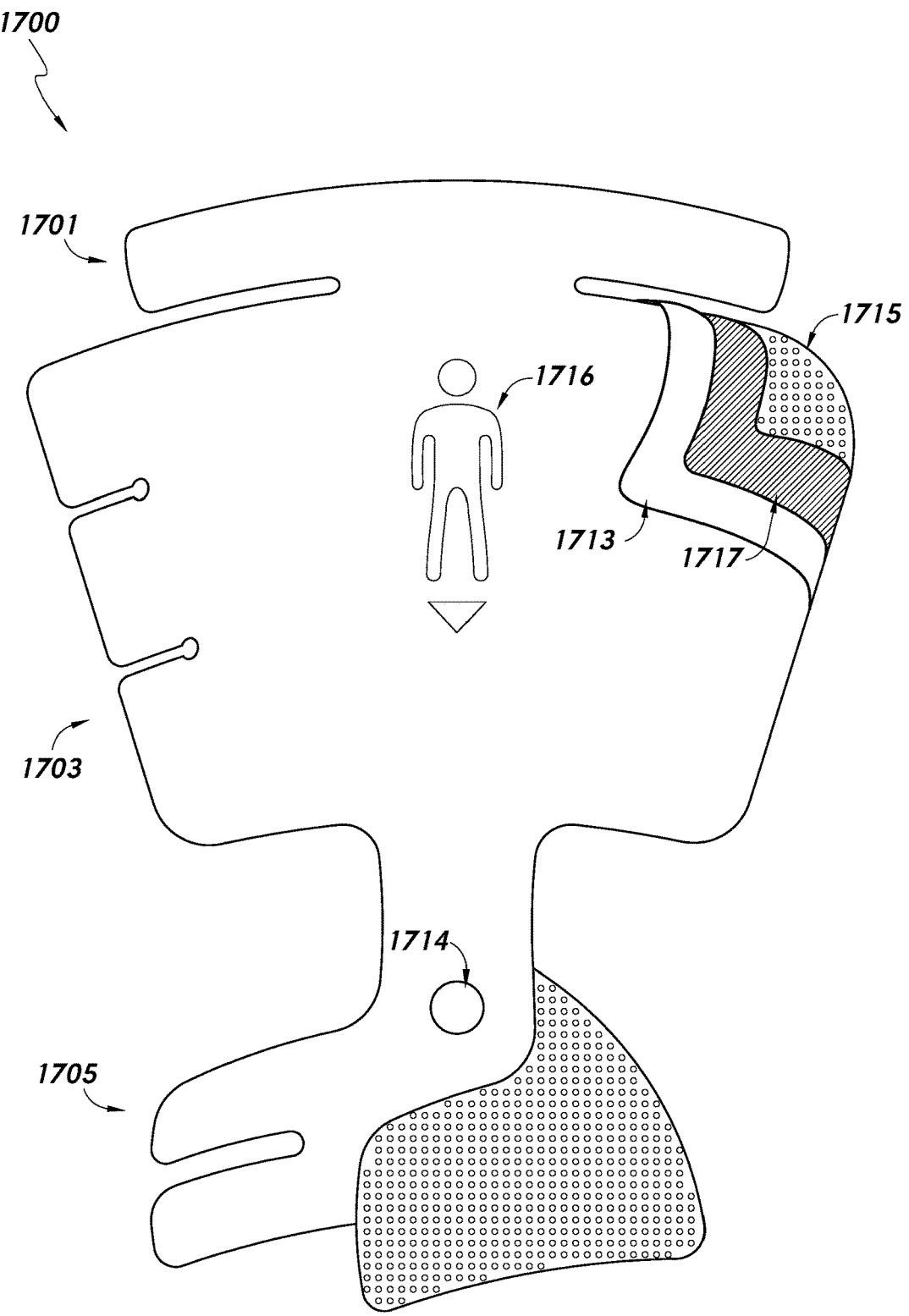
FIG. 17 illustrates an example sleeve comprising various physical, visible, and/or palpable anomalies or markers to improve the ease-of-use of the sleeve in accordance with one or more embodiments.

FIG. 17 illustrates an example sleeve 1700 comprising various physical, visible, and/or palpable anomalies or markers to improve ease-of-use of the sleeve 1700. In some embodiments, the sleeve 1700 may comprise a heel locator 1714 (e.g., a cavity and/or opening in the sleeve 1700) to indicate a specific anatomical placement for the patient's heel. Other anomalies and/or markers may include a cavity and/or opening in the sleeve 1700 for the patient's knee. The sleeve 1700 may include extendable and/or collapsible sections (e.g. dimensionally adjustable and/or elastic regions that enable the knee region, ankle, and foot region to be stretched to the desired length prior to application) within the sleeve 1700 body that may enable universal placement of a single-size sleeve 1700 on a majority of the adult patient population. In some embodiments, a sleeve 1700 may comprise one or more adhesive regions (including, e.g., self-adhering sections such as Velcro, buttons, etc.) to allow portions of the sleeve 1700 to adhere and/or attach to other portions of the sleeve 1700 to collapse and/or compress the sleeve 1700.

Various features of the sleeve 1700 may be configured to facilitate correct placement of the device to a patient's limb. Such features may include visual marks, surface variations, cavities for anatomical landmarks, and/or unique form factors. In some embodiments, the heel locator 1714 may comprise a hole, slit, or similar opening in the sleeve that is designed to be placed specifically around the heel. The heel locator 1714 may additionally or alternatively be marked by one or more visual indicators (e.g., text and/or graphics) that may be sufficiently distinguishable by the human eye. Such visual indicators may be included independently of, or in conjunction with, the described anatomical hole, slit, or similar opening. In some embodiments, placement features may be adapted to any of the knee, elbow, wrist, shoulder, and/or other key anatomical landmarks/features. In some embodiments, the sleeve 1700 may comprise differing materials, textures, and/or colors distinguishing between an inner surface 1713 (e.g., a skin-contacting surface) and an outer surface 1715 (e.g., an environment-facing surface).

In some embodiments, the sleeve 1700 may include an orientation indicator 1716 indicating correct orientation of the sleeve 1700 with respect to the patient and/or the patient's limb. The orientation indicator 1716 may be configured to indicate correct placement of the sleeve 1700. In some embodiments, a first portion 1701 and/or second portion 1703 of the sleeve 1700 may be larger in diameter than a third portion 1705 of the sleeve, as the first portion 1701 and/or second portion 1703 may be configured for placement over larger areas of the patient's limb (e.g., the thigh, knee, and/or calf) while the third portion 1705 may be configured for placement at the patient's foot and/or ankle. The orientation indicator 1716 may comprise one or more visual indicators, which may include text and/or graphics. In some embodiments, the orientation indicator 176 may be printed at an outer surface of the outer layer 1713. The outer layer 1713 and/or outer surface of the outer layer 1713 may comprise features configured to increase surface friction of the sleeve 1700 to prevent slipping. For example, the outer layer 1713 may comprise various materials (e.g., silicone strips) and/or textures printed and/or embedded into the outer layer 1713 and/or outer surface of the outer layer 1713 (e.g., at the third portion 1705 which may be configured to be placed over the sole of the foot) to increase surface friction.

The inner layer 1715 may comprise mesh or similarly breathable material. The outer layer 1713 may comprise any suitable material. In some embodiments, the outer layer 1713 may comprise one or more materials configured to attach to Velcro and/or other attachment materials and/or mechanisms. The sleeve may comprise a middle layer 1717 between the inner layer 1715 and the outer layer 1713. In some embodiments, the middle layer 1717 may comprise a wicking material and/or other at least partially breathable material. In some embodiments, the inner layer 1715 may be configured to contact a patient's skin and/or may be at least partially temperature-controlled. In some embodiments, the inner layer 1715, middle layer 1717, and/or outer layer 1713 may be configured to allow for layer deformation in support of deep vein thrombosis (DVT) prophylaxis.

Figure 18:
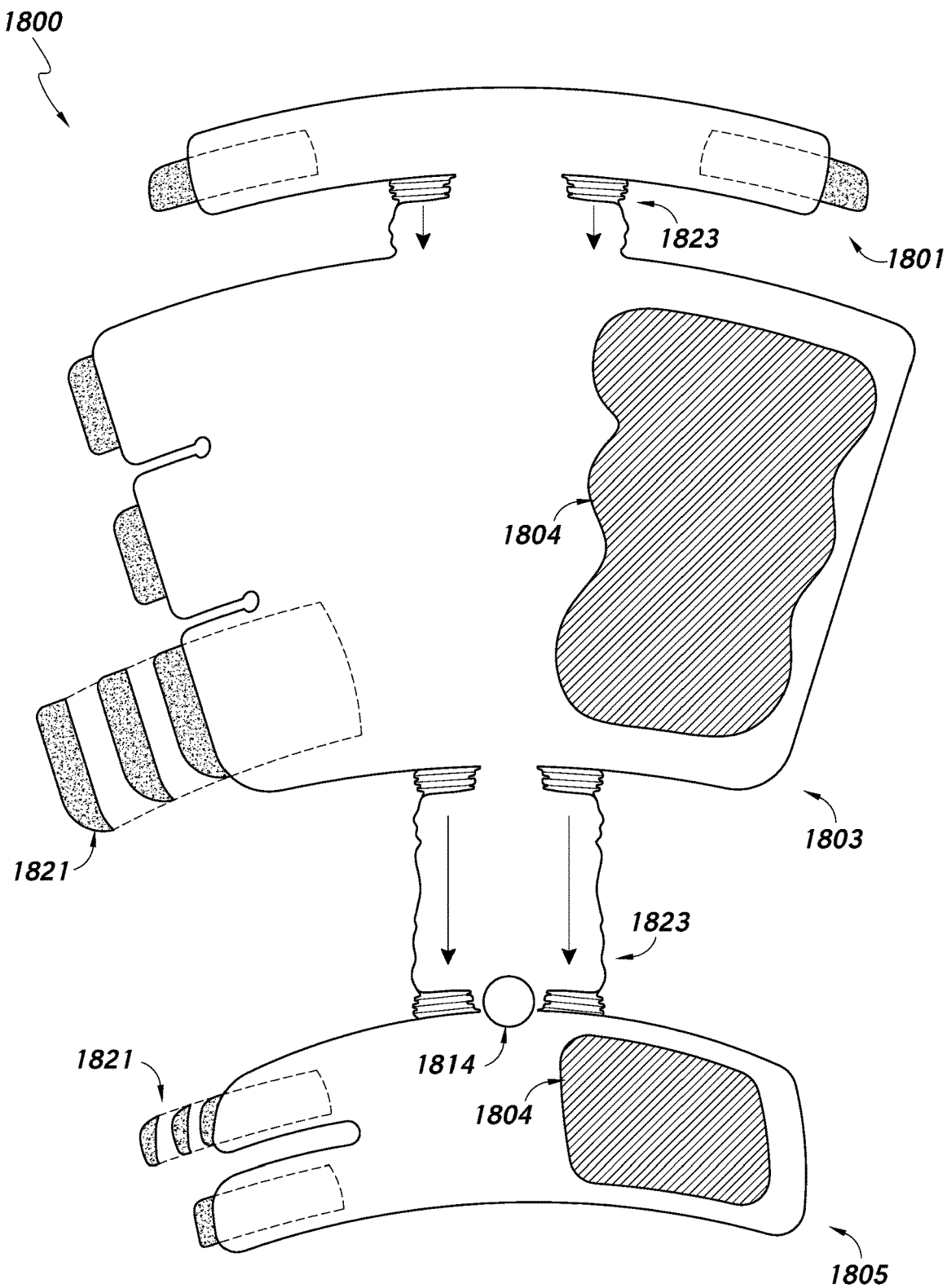
FIG. 18 illustrates an adjustable sleeve configured to provide heating and/or compression to one or more areas of a patient's body in accordance with one or more embodiments.

FIG. 18 illustrates an adjustable sleeve 1800 configured to provide heating and/or compression to one or more areas of a patient's body. The sleeve 1800 may comprise one or more compression elements 1804, which may include inflatable bladders. In some embodiments, the sleeve 1800 may be configured to deliver pneumatic sequential compression of various target areas (e.g., the calf and/or foot). The sleeve 1800 may be configured to receive pneumatic (e.g., heated) gas and/or other fluid for conductive heat transfer in support of core body temperature regulation. In some embodiments, temperature and/or pressure regulation functionality for the sleeve 1800 may be managed at a controller (e.g., 50.5C exiting the controller, 40 mmHg/130 mmHg feedback).

The sleeve 1800 may be configured to provide compression and/or heating to one or more of the patient's thigh (or at least above-the-knee areas of the patient's leg), knee, calf, and/or foot. The one or more compression elements 1804 may be configured for placement at, for example, the calf and/or sole of the foot. The compression elements 1804 may be configured to be sequentially inflated and/or deflated to compress the tissue and drive venous return. In some embodiments, the sleeve 1800 comprises a compression element configured to be positioned behind the knee to provide a heated surface to the popliteal fossa.

Gas and/or fluid provided to the sleeve 1800 may be heated within a controller or associated device to a specified temperature set point before delivery to the sleeve 1800. In some embodiments, the fluid may be selectively heated so that only compression elements 1804 covering certain target areas (e.g., the sole of the foot and/or popliteal fossa) may be elevated in temperature to reduce power requirements. Heat control may be open-loop (e.g., toggled on-off and to specified temperatures by a clinician) or closed-loop from an external temperature probe (e.g., core body temperature—esophageal, tympanic, etc.).

In some embodiments, the sleeve 1800 may be configured to inflate and/or deflate in multiple sequences. For example, an inflation/deflation sequence of the sleeve 1800 at a first portion 1801 and/or third portion 1805 may be different from the inflation/deflation sequence of the sleeve 1800 at a second portion 1803. In some embodiments, to maintain surface contact with the skin tissue, one or more compression elements 1804 may not completely deflate. For example, to avoid restricting blood flow, a compression element 1804 configured to be placed at or near a knee of a patient may have a lower maximum pressure compared to compression elements 1804 configured for placement at a calf and/or foot portion of the patient. Inflation/deflation cycles may be relatively rapid (e.g. every 10 seconds) to maintain high temperatures. It should be understood that, as with any of the other embodiments disclosed herein, in some implementations, the knee portion 1801 and foot portion 1805 do not have compression bladder(s) and/or are not designed for compression therapy, whereas the calf portion 1803 includes one or more compression bladders or other compression components.

In some embodiments, the compression elements 1804 may comprise one or more pneumatic bladders configured to adjust the position of the sleeve 1800 and lower limb for optimal heat transfer. The sleeve 1800 may comprise one or more perforated channels or areas used to provide convective heat transfer to various target areas (e.g., the popliteal fossa and foot sole) in support of core body temperature regulation. The one or more perforated channels may be patterned into the sleeve 1800 (e.g., at the sole of the foot and the back of the knee) for heat transfer. In some embodiments, the sleeve 1800 may comprise additional compression/bladder elements (e.g. above the knee and/or at the heel and/or ball of the foot) to provide spacing of the one or more perforated channels away from the skin (e.g., to allow convective flow).

The compression elements 1804 may be inflated/deflated according to pressure sequences that may be advantageous for DVT prophylaxis (e.g., approximately one minute on-off cycle). The gas and/or fluid in the compression elements 1804 may be heated and/or may be uncontrolled for temperature. The inflation level of the compression elements 1804 may be controlled by pressure sensors located in a controller.

One or more of the compression elements 1804 may be utilized as supporting bladders for one or more warming elements. Accordingly, one or more compression elements 1804 may be inflated to a lower pressure than other compression elements 1804 to provide spacing but not cut off blood flow. The compression elements 1804 may be inflated when heating is turned on and/or may be deflated when no heating is required.

One or more perforated channels may be provided with heated gas (e.g., air) by a controller. When in heating mode, the controller may provide a continuous supply of heated gas at a defined set point. Gas and/or fluid temperature may be monitored/controlled using a temperature sensor (e.g., thermocouple, resistance temperature detector, thermistor, etc.) residing in the controller device. The flow rate of the gas and/or fluid may be tuned to match the perforations of the sleeve 1800 so that the channels may be continuously in a partially inflated state.

Temperature regulation of the gas and/or fluid may be manually controlled by a clinician (e.g., using an on/off toggle) and/or automatically via an external temperature probe (e.g., providing information about core body temperature).

In some embodiments, the compression elements 1804 may be circumferential or non-circumferential. For example, compression elements 1804 utilized as supporting bladders may take the form of a "pillow" that may not wrap entirely around the patient's limb but may instead protrude at or near one or more outer edges of the sleeve 1800. The sleeve 1800 may comprise one or more supporting bladders that may be composed of a compressible material (e.g., foam). Such supporting bladders may not utilize intermittent compression unlike other compression elements 1804.

One or more target areas of the patient's body may be heated and/or compressed using a single channel or multiple channels. For example, an area behind the knee and the sole of the foot may be heated using a single channel or may be independently operated. In some embodiments, temperatures at different portions of the sleeve may be independently adjustable.

The sleeve 1800 may be configured to apply heating at various target areas (e.g., the popliteal fossa and sole of the foot) using, for example adhered heating patches which have any of a variety of forms. For example, the sleeve 1800 may comprise (1) an inflatable heating bladder for fluid-based, conducting heating. (2) a wire-based patch for resistive, conductive heating. (3) a battery-operated, wireless patch for resistive, conductive heating, and/or (4) a topical chemistry configured to generate an exothermic reaction for chemical, conductive heating. Heating patches may be configured to be adhered directly to the skin (e.g., forming an air-tight and/or water-tight seal). Some embodiments may involve the heating patches being placed and/or attached as an additional piece to a DVT prophylaxis sleeve, and/or may be positioned separately as independent sleeves/wraps. In some embodiments, temperature sensors may be integrated into heating patches and/or may reside within a controller. In the case of chemical application, no temperature sensor may be required.

In some embodiments, the sleeve may be configured to be adjustable to varying sizes to accommodate varying sizes of patients' limbs. However, a single size may be manufactured with features enabling the placement of the sleeve 1800 across a wide range of anatomical sizes. The sleeve 1800 may have adjustable features including tightening straps 1821 and/or collapsible/extendable regions 1823. The adjustable features may be situated either along the entire device or in specific segments along the device and/or may allow universal placement of a single sleeve 1800 design. For example, in one embodiment, a third portion 1805 area of the device immediately proximal to a heel locator 1814 may be intentionally oversized in length so that it may be configured to be folded upon itself to accommodate limbs of different lengths. In some embodiments, the third portion 1805 may contain a clasp or adhesive feature to hold the excess material, if any, in place. The third portion 1805 may be replaced by a material with dynamic physical properties that can enable the device to elongate and accommodate limbs of different lengths and/or sizes. For example, at least a portion of the sleeve 1800 may be configured for two-way (i.e., single-axis) and/or four-way (multi-axis) stretching. In such an embodiment, the sleeve 1800 may have a greater elongation in the vertical direction than the horizontal direction. Varying elasticity or elongation properties of the device or specific segments of the device may be manufactured from the same or different material with same or different material properties as the remaining portion(s) of the sleeve 1800.

The sleeve 1800 may comprise various fixation elements which may be utilized for intuitive placement through the unique placement, shape, materiality, and color of the fixation elements. In some embodiments, a first portion 1801 may be placed above, below, or circumferentially around a knee with a form factor such that when pulling the strap superiorly and around the kneecap, the strap may secure only horizontally around the kneecap and not at an angle. In this way, a first arm of the first portion 1801 may be configured to at least partially overlap with a second arm of the first portion 1801. In some embodiments, the first portion 1801 may be configured to create force based at least in part on the angle of placement at the patient's limb. For example, the angle of placement of the first portion 1801 may be configured to prevent an upper edge of the sleeve 1800 from sliding down the patient's limb. The sleeve 1800 may comprise a plurality of wraps that can be applied to a patient's limb whereby each one of the pluralities of wraps may further comprise tightening straps 1821. In some embodiments, individual compression elements 1804 may not be joined along their full lengths so that when they are applied, one can be crossed over the other, as to allow the angulation of the application of the upper bladder to accommodate the calf area horizontally.

In some embodiments, the sleeve 1800 may be configured to be placed using a combination of fixation members and/or self-fixating regions. The sleeve 1800 may comprise multiple independent circumferentially closed, self-fixating regions that can be applied directly over the entire limb and pulled up to the desired location on the limb. The sleeve 1800 may be configured to self-contract or expand so as to maintain sufficient contact with the limb and remain sufficiently fixated in position. In some embodiments, the sleeve 1800 may be entirely circumferentially closed with no additional fixating members.

Interfacing Between Limb Sleeve and Control Unit

Figure 19:
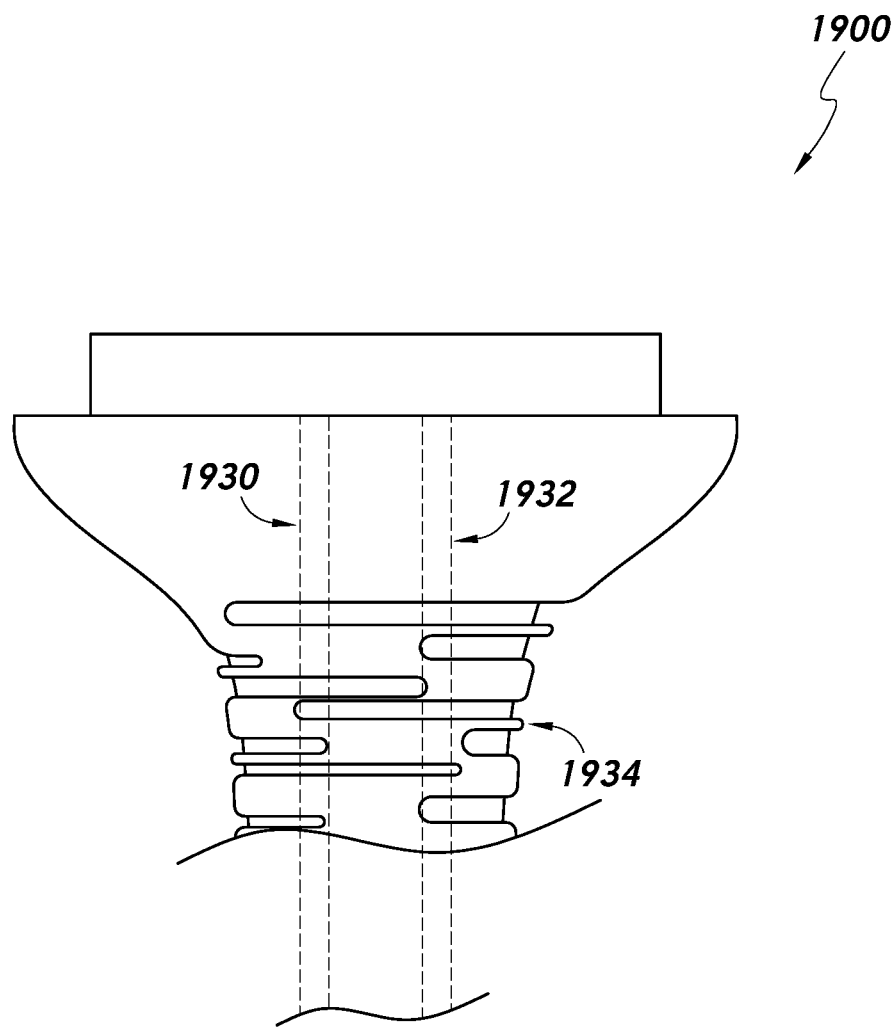
FIG. 19 illustrates an interface for connecting one or more sleeves to a controller in accordance with one or more embodiments.

FIG. 19 illustrates an interface connector 1900 for connecting one or more sleeves to a controller. The interface 1900 may be configured to attach between a sleeve and the controller such that the interface 1900 can maintain a hermetic seal for delivering one or more channels, which may include an internal fluid channel 1930 and/or an electric channel 1932. The interface 1900 may be configured to maintain the hermetic seal to the external environment. In some embodiments, the interface 1900 may be configured to be attached in either of multiple possible fixation orientations or in a single orientation.

In some embodiments, inflation level of one or more compression elements at a sleeve may be controlled by pressure sensors located in a controller and the sleeve. Fluid temperature may be monitored and/or controlled using a temperature sensor (e.g., a thermocouple, RTD, thermistor, etc.) residing in the controller and/or the sleeve. In some embodiments, temperature regulation may be manually controlled by a user and/or automatically via an external temperature input. The interface 1900 may comprise a neck portion 1934 configured to be bent. For example, the neck 1934 may have built-in slack to allow for bending.

The neck portion 1934 may protect one or more of an electrical line 1930 and a fluid line 1932, which may provide for the reception and/or transmission of electric signals (e.g., data and/or power) and/or fluid (e.g., fluid pumping and/or provision). The neck portion 1934 may be configured to bend along one axis, two axes, or three or more axes. The connector 1900 may be a component of a sleeve or a connector.

FIG. 20 illustrates sleeves 2000 comprising electrical and/or fluid connectors 2016 configured to connect to a controller via an interface. The sleeves 2000 may comprise various electrical cabling components, which may include one or more cabling components (e.g., two) per warming element and/or one or more cabling components (e.g., two) per temperature sensor (e.g., thermistor). The cabling components may be routed within the sleeve 2000 with enough length to provide strain relief for any stretch and/or bending applied to the sleeve 2000. Additional sleeve alignment features may be welded or otherwise attached/coupled in place to guide the cabling to preferred areas in the sleeve 2000. The alignment features may be configured to keep cabling away from pressure points (e.g., the patient's heel).

Cable routing may be designed to maximize patient comfort, minimize interference during a procedure, and/or minimize risk of injury (e.g., while the patient is mobile). For example, a foot sleeve may comprise a cable exiting next to the heel and/or a knee sleeve may comprise a cable exiting towards the heel. Cables may be bundled together to form a single cable per leg.

In some embodiments, one or more arms of the sleeve 2000 may be configured to be welded and/or otherwise attached to compression elements and/or compression sleeves. In some embodiments, multiple arms joined together may form a compression element above and/or below the kneecap of the patient.

FIGS. 21A and 21B illustrate systems including one or more cables, wires, and/or tubes 2140 (referred to individually and/or collectively in the following description as "cable components") connecting a sleeve 2100 to a controller 2150. In some embodiments, fluid provided to the sleeve 2000 via the cable component(s) 2140 may be heated within the controller 2150 to a specified temperature before delivery to the sleeve 2100. The fluid may be selectively heated so that only bladders at the sleeve 2100 covering specific anatomical regions may be temperature modulated. In some embodiments, temperature control of the warming therapy may be open-loop (e.g., manually specified temperatures) or closed-loop (e.g., automatically controlled to maintain the desired temperature profile, such as in response to a sensor (e.g., temperature, pressure, etc.) feedback). For example, temperature feedback may be generated and/or provided relating to any of esophageal, tympanic, oral, inguinal urinary, and rectal temperatures.

In the illustrated configuration/embodiment of FIG. 21A, the connector 2101 is associated with a distal end of the cable 2140, which is coupled to or integrated with the sleeve device 2100a, whereas in the illustrated configuration/embodiment of FIG. 21B, a connector associated with a distal end of a cable 2140b that is coupled to or integrated with the controller 2150b is connected to a corresponding connector 2102 of the sleeve 2100b. In some embodiments, a cable is used that has connectors at both ends thereof, wherein one of the connectors is configured to connect to a corresponding connector of a sleeve device and the other connector is configured to connect to a corresponding connector of a controller device.

Temperature management controllers and/or control circuitry, such as embodiments of the controllers 2150 in FIGS. 21A and 21B, may be configured to perform any type of functionality relating to the control of the devices 2100. For example, temperature management device control implemented in any of the embodiments of the present disclosure may include control related to any of the devices, systems, and/or processes disclosed in U.S. patent application Ser. No. 16/777,895, filed Jan. 31, 2020, and entitled REAL-TIME BODY TEMPERATURE MANAGEMENT, the disclosure of which is hereby expressly incorporated by reference in its entirety and constitutes part of the present disclosure.

Figure 22:
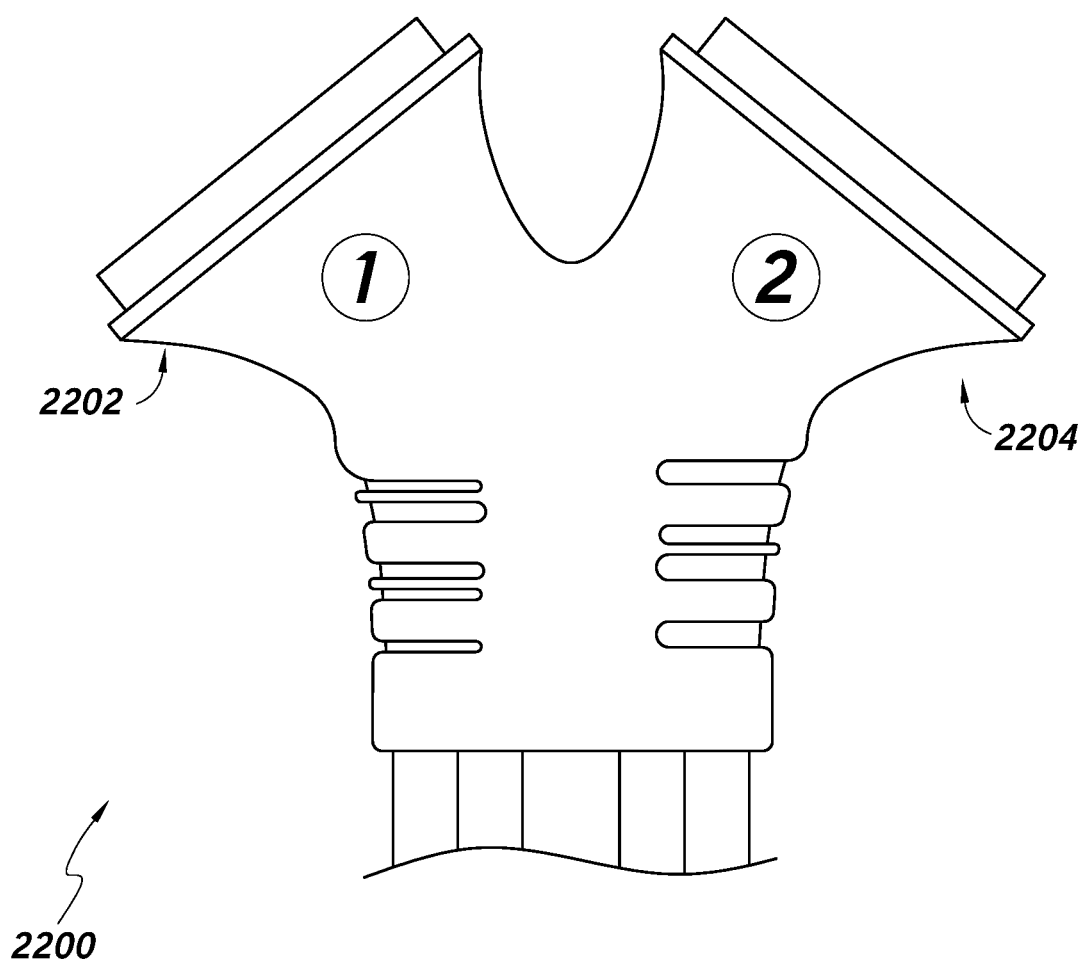
FIG. 22 illustrates a multi-channel interface for connecting one or more sleeves to a controller in accordance with one or more embodiments.

FIG. 22 illustrates a multi-channel interface 2200 for connecting one or more sleeves to a controller. The multi-channel interface 2200 may comprise at least two sections and may be configured to separate the heat delivery to a first channel 2202 and compression (e.g., fluid) delivery to a second channel 2204. In some embodiments, the interface 2200 may comprise at least two independent interface components, wherein each interface may be reserved for the same energy transferring channel types (e.g., heating or fluid) or a mix of both energy transferring channel types (e.g., heating and fluid). The multi-channel interface 2200 may comprise physical latching features to allow the patient contacting portion of the interface 2200 to be connected and disconnected with the sleeve. In some embodiments, the multi-channel interface 2200 may be an asymmetric interface and/or may include other physical and/or visual features designed to prevent the incorrect mating of the at least two separate portions of the interface. The interface 2200 may comprise physical design characteristics such that either fluid or heat transferring channels may be excluded in the final interface connection, as chosen by a user.

Additional Possible Implementation Details

In some embodiments described herein, a system/device may be configured to manage core body temperature via compression and warming. Warming may be applied to at least the popliteal fossa and sole of the foot of a patient. In some embodiments, warming may be delivered via conductive means, mainly by the use of resistive heating or a fluid-warmed bladder. The contact between the conductive heating element and the patient limb may be maintained through the use of a limb-biasing apparatus (e.g. foam, bladder, or strap positioned between the heating element and the outer sleeve layer, wherein upon inflation or application, surface contact between the heating element the leg and the leg is created and/or maintained). In some embodiments, limb-biasing feature may be used for warming methods other conductive heat transfer. For example, warming bladders may be configured to create a pocket/cavity to direct temperature-controlled fluid and/or gas to a patient's skin.

Warming may be delivered via convective means, mainly by a system to provide pressurized, thermally treated gas to a convective warming device by way of an air-tight and/or water-tight hose. The system may comprise a forced gas warming unit for providing a stream of pressurized warm gas (e.g., 27° C.-50.5° C.) through channels or bladders within the sleeve. The system may further comprise a heater in the forced-air warming unit, a control circuit in the forced air warming unit, and/or a limb sleeve with perforation connected to the forced-air warming unit In some embodiments, warming temperature may be cyclical so as to avoid burning of the skin. One or more heating elements may be configured to deliver heat in a controlled manner (e.g., via pulse-width modulation). In some embodiments, a heat application cycle may be synced (with some offset) in time to the cycles of compression. Compression may be applied to at least the calf of a patient.

Some embodiments may involve a method of intuitively placing a limb sleeve. The sleeve may comprise one or more physical, visible, and/or palpable anomalies or markers in the sleeve structure that indicate unique anatomical placement (e.g., a hole for knee and heel) and/or orientation (e.g., patient-facing surfaces). In some embodiments, a sleeve may comprise extendable and/or collapsible sections within the sleeve body that enable universal placement of single size sleeve (e.g. dimensionally adjustable and/or elastic regions that may enable the knee region, ankle, and foot region to be stretched to a desired length prior to application).

A universal interface connector may be situated between the sleeve and controller. The interface may be configured to maintain a hermetic seal between the internal fluid and electric channels. In some embodiments, the interface may be configured to maintain a hermetic seal to the external environment. The interface can be attached in a single or multiple fixation orientations. For example, the interface may be configured to maintain a hermetic seal with only one of the internal fluid and electric channels.

In some embodiments, a connector interface may comprise multiple (e.g., three) air-tight and/or water-tight channels, multiple (e.g., two) heating channels, multiple (e.g., two) sensor/feedback channels, and/or at least one ground channel. The interface may comprise one connector per sleeve to support a compression element, heating elements, and/or temperature sensors. A compression channel may take the form of multiple (e.g., three or more) air-tight and/or water-tight channels. Heating, sensor, and/or ground channels may be watertight. In some embodiments, heating, sensor, and/or ground channels may be configured to provide electrical connection achieved through conducting pins to either of multiple configurations. A controller may be situated on one end and a connecting cable may be situated on a second end. In other embodiments, a connecting cable may be situated on one end and a sleeve may be situated on a second end. In some embodiments, a controller may be situated on one end and a sleeve may be situated on a second end.

A connector may comprise multiple (e.g., two) regions separating air-tight and water-tight regions. Air-tightness may be achieved through an O-ring and/or nozzle and/or hose interface for each channel. Water-tightness may be achieved through an O-ring for the entire watertight compartment. In some embodiments, a connector may comprise physical latching features to allow the connector and parts to be connected (i.e., joined) or disconnected (i.e., separated) easily. The connector may comprise an asymmetric interface and/or other physical features designed to prevent incorrect orientation in the connection between controller, cable, and/or sleeve. In some embodiments, the connector may comprise visual locating features to assist in orientation and/or implementation/removal of the air-tight/water-tight connection between controller, cable, and/or sleeve. The connector may comprise physical design characteristics such that either compression or heating may be excluded (optional components) on the cable/sleeve connection side.

In some embodiments, a connector may comprise a single compartment encompassing both air-tight and watertight regions such that air-tightness may be achieved through O-ring and/or nozzle/hose interface for each air-tight channel. Water-tightness may be achieved through an O-ring around the entire compartment. The connector may comprise two independent components (e.g., one each of compression and heating) that may be optionally joined by cabling or within the sleeve.

A controller may comprise one or more temperature monitors configured to determine gas (e.g., air) temperature as the gas enters the hoses on the way to the sleeve. In some embodiments, the controller may utilize an on/off switch set at approximately 43° C. A conductive channel may be utilized to support temperature sensors.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including." "having." and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X. Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment. Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

Although certain preferred embodiments and examples are disclosed below, inventive subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The spatially relative terms "outer." "inner," "upper," "lower," "below," "above," "vertical," "horizontal." and similar terms, may be used herein for ease of description to describe the relations between one element or component and another element or component as illustrated in the drawings. It be understood that the spatially relative terms are intended to encompass different orientations of the device in use or operation, in addition to the orientation depicted in the drawings. For example, in the case where a device shown in the drawing is turned over, the device positioned "below" or "beneath" another device may be placed "above" another device. Accordingly, the illustrative term "below" may include both the lower and upper positions. The device may also be oriented in the other direction, and thus the spatially relative terms may be interpreted differently depending on the orientations.

Unless otherwise expressly stated, comparative and/or quantitative terms, such as "less," "more," "greater." and the like, are intended to encompass the concepts of equality. For example, "less" can mean not only "less" in the strictest mathematical sense, but also, "less than or equal to."

What is claimed is:

1. A system for maintaining normothermia via compression and warming, the system comprising: a first wearable portion configured to cover a sole of a foot of a patient's leg, the first portion having associated therewith a first warming element positioned and configured to apply warming to the sole of the foot; a second wearable portion coupled to the first wearable portion and configured to cover a calf of the patient's leg, the second wearable portion having associated therewith a compression element; and a third wearable portion coupled to the second wearable portion and configured to cover a popliteal fossa of the patient's leg, the third wearable portion having associated therewith a second warming element positioned and configured to apply warming to a popliteal fossa, the second warming element comprising a fluid bladder configured to receive heated fluid through a fluid channel that passes through at least a portion of the second wearable portion, the fluid bladder having a plurality of perforations on a patient-facing side thereof configured to pass the heated fluid from the fluid bladder to skin of the popliteal fossa; wherein the fluid bladder has a greater width than the fluid channel; wherein the fluid bladder is surrounded by a border having a reduced thickness relative to adjacent portions of the third wearable portion, the border being configured such that the border does not contact the popliteal fossa when the third portion covers the popliteal fossa.

2. The system of claim 1, wherein the fluid channel fluidly couples the fluid bladder to one or more compression bladders of the compression element.

3. The system of claim 1, wherein contact between the second warming element and the popliteal fossa is maintained by a foam insert disposed in the first wearable portion and configured to press the fluid bladder against skin of the popliteal fossa.

4. The system of claim 1, wherein the third wearable portion comprises one or more support portions adjacent to the second warming element and configured to be inflated with fluid to maintain a cavity between the second warming element and the popliteal fossa to reduce a risk of burning skin of the patient.

5. The system of claim 4, wherein the one or more support portions provide a space for convective heat transfer from the heated fluid.

6. The system of claim 1, wherein the compression element comprises one or more compression bladders.

7. The system of claim 6, wherein the fluid bladder of the third wearable portion is fluidly isolated from the one or more compression bladders of the second wearable portion.

8. The system of claim 7, wherein the one or more compression bladders are configured to be filled with non-heated air when the heated fluid is disposed in the fluid bladder of the third wearable portion.

9. The system of claim 8, wherein the system is configured to cycle the heated fluid in the fluid bladder at a higher frequency than fluid is cycled in the one or more compression bladders.

10. The system of claim 1, further comprising a multi-channel interface configured to receive compression fluid and the heated fluid through separate fluid channels.

* * * * *